(12) United States Patent
Heath et al.

(10) Patent No.: US 9,924,911 B2
(45) Date of Patent: Mar. 27, 2018

(54) TOMOSYNTHESIS COLLIMATION

(71) Applicant: Carestream Health, Inc., Rochester, NY (US)

(72) Inventors: Michael D. Heath, Rochester, NY (US); Xiaohui Wang, Pittsford, NY (US); Dennis J. O'Dea, Farmington, NY (US)

(73) Assignee: Carestream Health, Inc., Rochester, NY (US)

( * ) Notice: Subject to any disclaimer, the term of this patent is extended or adjusted under 35 U.S.C. 154(b) by 190 days.

(21) Appl. No.: 15/064,677

(22) Filed: Mar. 9, 2016

(65) Prior Publication Data

US 2016/0270745 A1   Sep. 22, 2016

Related U.S. Application Data

(60) Provisional application No. 62/135,289, filed on Mar. 19, 2015.

(51) Int. Cl.
| A61B 6/06 | (2006.01) |
| A61B 6/02 | (2006.01) |
| G21K 1/02 | (2006.01) |
| H05G 1/00 | (2006.01) |
| A61B 6/00 | (2006.01) |

(52) U.S. Cl.
CPC ............... *A61B 6/06* (2013.01); *A61B 6/025* (2013.01); *A61B 6/4007* (2013.01); *G21K 1/02* (2013.01); *H05G 1/00* (2013.01); *A61B 6/4021* (2013.01)

(58) Field of Classification Search
CPC ......... A61B 6/025; A61B 6/06; A61B 6/4007; A61B 6/4021; G21K 1/02; H05G 1/00
See application file for complete search history.

(56) References Cited

U.S. PATENT DOCUMENTS

| 7,505,562 | B2 | 3/2009 | Dinca et al. |
| 8,172,633 | B2 | 5/2012 | Park et al. |
| 2006/0227131 | A1 | 10/2006 | Schiwietz et al. |
| 2010/0091939 | A1 | 4/2010 | Fadler |
| 2011/0003109 | A1 | 1/2011 | Slinker et al. |

(Continued)

FOREIGN PATENT DOCUMENTS

WO    WO 2014/116665    7/2014

OTHER PUBLICATIONS

Je Hwang Ryu et al., "Carbon Nanotube Electron Emitter for X-ray Imaging," Materials, May 2012, pp. 2353-2359.

(Continued)

*Primary Examiner* — Mark R Gaworecki

(57) ABSTRACT

A radiographic imaging apparatus having a detector, a radiation source array, and a control processor is configurable to individually energize the radiation sources. A collimator having a number of apertures is movable to either a first or second position in a path of the radiation source array. In one position, the apertures are aligned with a first subset of the radiation sources. In another position, the apertures are aligned with a second subset of the radiation sources. The second subset of the radiation sources define substantially the same radiation field that is defined by the first subset of the radiation sources. A transport apparatus translates the collimator member between at least the first and second positions according to an electronic instruction.

20 Claims, 32 Drawing Sheets

(56) References Cited

U.S. PATENT DOCUMENTS

2012/0257710 A1* 10/2012 Funk ................... A61B 6/4488
378/9
2015/0377803 A1* 12/2015 Turner ................. G01N 23/203
378/41

OTHER PUBLICATIONS

Jonathan S. Maltz et al., "Fixed gantry tomosynthesis system for radiation therapy image guidance based on a multiple source x-ray tube with carbon nanotube cathodes," 2009, Med. Phys., 36 (5), pp. 1624-1636.
Partial European Search Report for EP Application No. 16160733.8 dated Aug. 30, 2016, 2 pages.

* cited by examiner

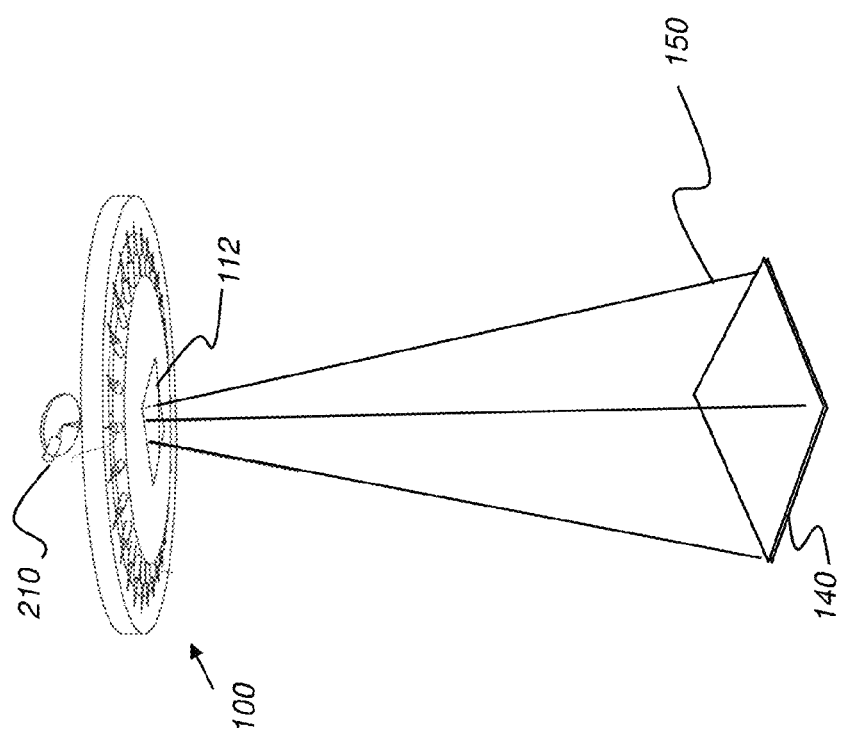

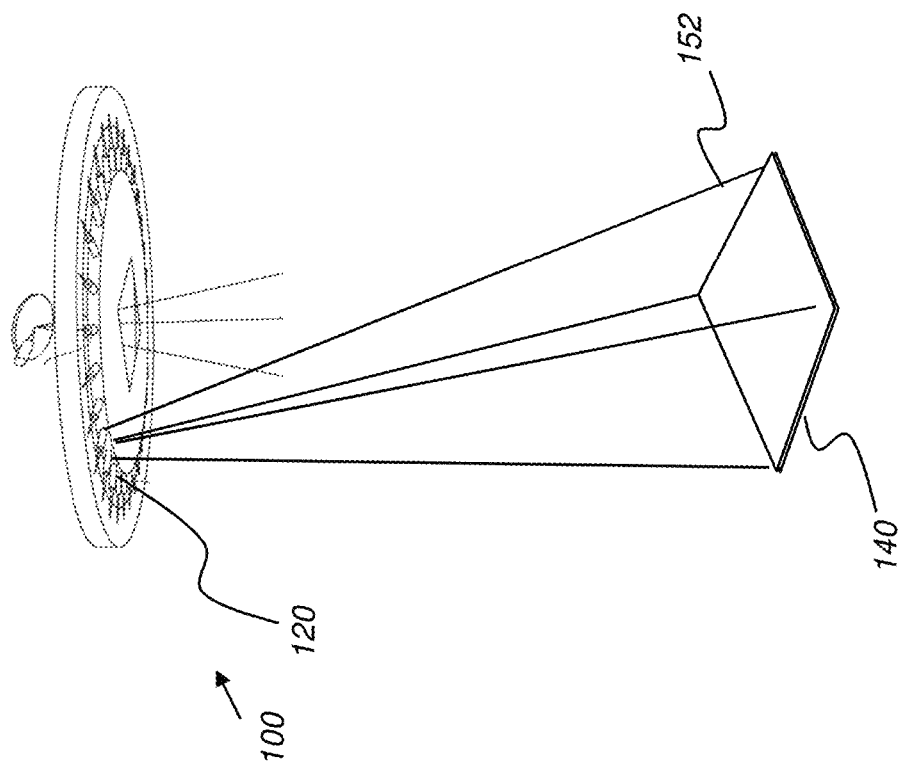

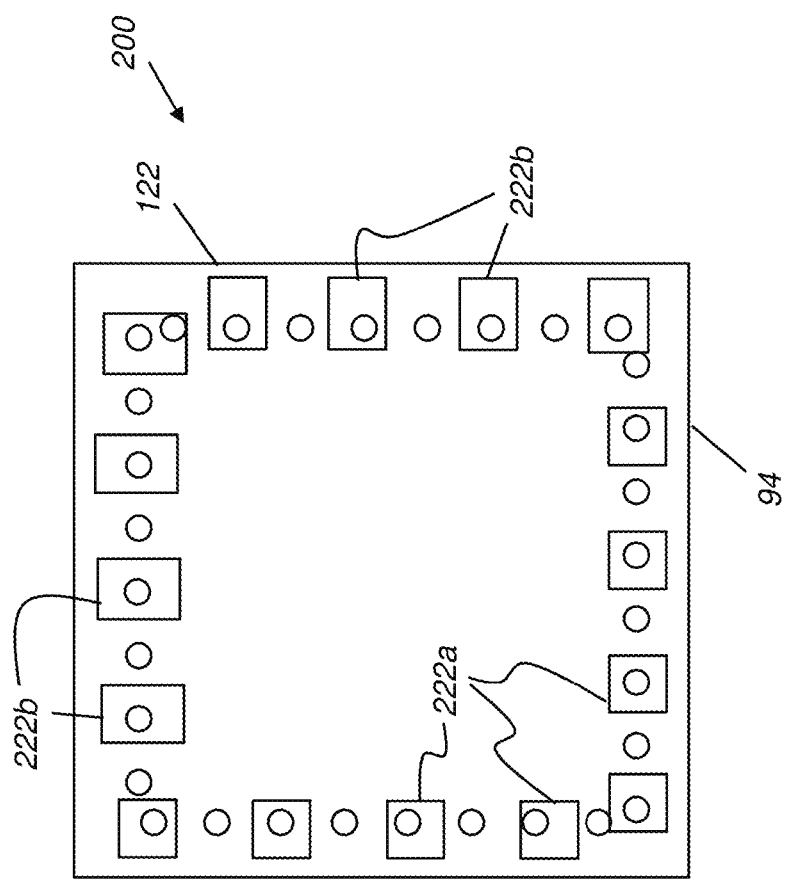

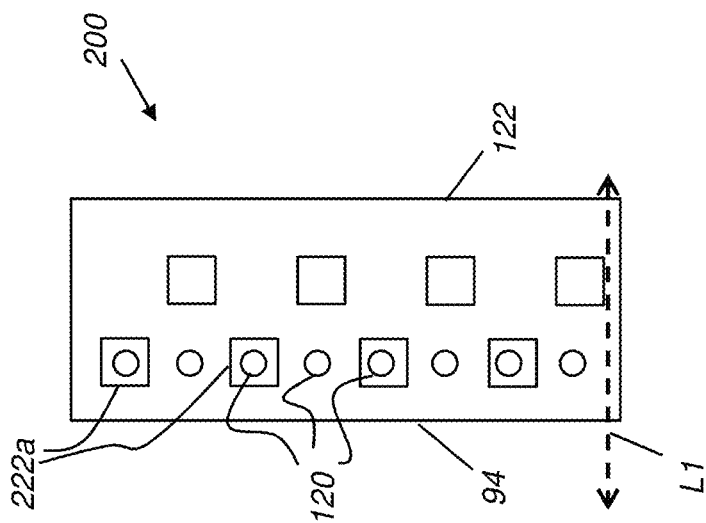

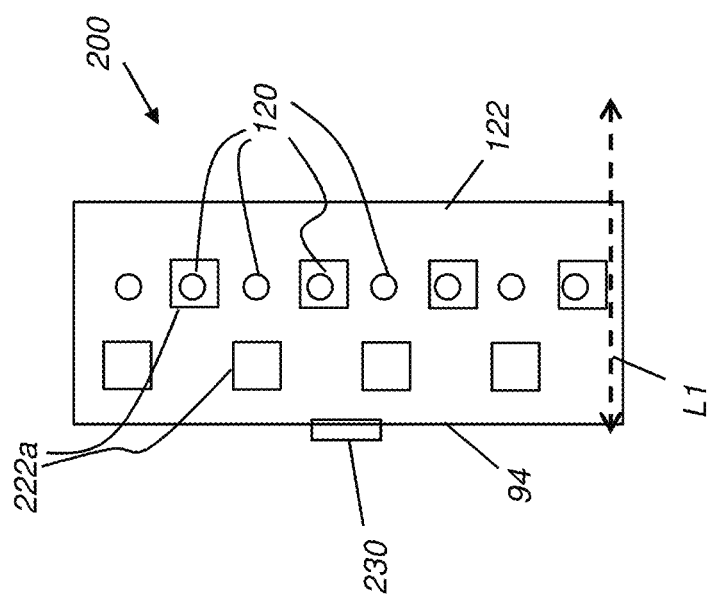

TOMOSYNTHESIS COLLIMATION

CROSS REFERENCE TO RELATED APPLICATIONS

This patent application claims priority to U.S. Provisional Patent Application Ser. No. 62/135,289 entitled TOMOSYNTHESIS COLLIMATION, filed Mar. 19, 2015.

Reference is made to commonly assigned International Patent Application No. PCT/US2014/012493 entitled "Directed X-ray Fields for Tomosynthesis" having a filing date of Jan. 22, 2014, and U.S. patent application Ser. No. 15/054,493 entitled "Hybrid Imaging Apparatus and Methods for Interactive Procedures" filed Feb. 26, 2016, which are both incorporated herein by reference in their entirety.

TECHNICAL FIELD

The disclosure relates generally to the field of radiography and more particularly to apparatus and methods for providing collimation for a distributed array of X-ray sources.

BACKGROUND

Tomosynthesis combines digital image capture and processing with some portion of the source/detector motion available in 3-D tomography to provide a measure of depth information from an imaged subject. By contrast with computed tomography (CT), digital tomosynthesis uses a small rotation angle, typically between 20° and 40°, with images acquired by varying the orientations of the x-ray tube relative to the patient and detector with a small number of discrete slices/exposures (e.g., 10 exposures). This is usually accomplished by either moving both the detector and x-ray source or by fixing the position of the detector and moving the x-ray source. In applications where the detector is fixed, multiple spatially distributed X-ray sources may be used or one or more movable sources may be discretely displaced and fired in various imaging patterns or trajectories.

The set of image data that is acquired, which is partial with regard to full volume image information, is digitally processed to yield an image similar to tomography but with a limited depth of field. Depth data is reconstructed from the captured projections in the form of a number of slices through the patient anatomy, with the best resolution from each slice taken parallel to the detector plane. A consequence of limited angular scanning for imaging used to reconstruct a 3-D object is that the in depth resolution is characteristically lower than the in-plane resolution of the reconstructed object. Since the image is digitally generated and represented, various processing techniques can be used to generate and present a series of slices at different depths and with different thicknesses reconstructed from the same image acquisition, thereby saving time and reducing radiation exposure.

Because the tomosynthesis data that is acquired is incomplete in terms of full three dimensions of data content, tomosynthesis does not offer the narrow slice widths and enhanced depth definition that CT offers. However, tomosynthesis provides high in-plane resolution and is advantaged over 2-D radiography by providing a measure of depth detail that is not otherwise available with conventional radiography.

A tomosynthesis imaging apparatus may have any of a number of source-detector arrangements for image acquisition. In a distributed array configuration, an array of X-ray sources may be disposed in a generally circular or other geometric distribution. Such a distribution may surround a central X-ray source that may include a standard radiography source, or the distribution may be arranged as a linear or curved path. Distributions of carbon nanotube (CNT) cathode X-ray sources may be arranged to provide tomosynthesis imaging without the need to reposition either the radiation source or the detector. Reference is made to an article by Je Hwang Ryu, Jung Su Kang, and Kyu Chang Park, entitled "Carbon Nanotube Electron Emitter for X-ray Imaging" in *Materials,* 2012, 5, 2353-2359 which is incorporated herein by reference in its entirety for nonessential background information. Reference is also made to U.S. Pat. No. 8,172,633 to Park et al., filed Apr. 4, 2007; U.S. Patent Application Publication No. 2011/0003109 by Slinker et al., filed Jul. 1, 2009; and U.S. Pat. No. 7,505,562 to Dinca et al., filed Apr. 19, 2007, which are incorporated herein by reference in their entireties.

One difficulty with distributed source arrangements relates to the need for appropriate collimation of emitted radiation. Among its functions, collimation controls the spread of radiographic energy so that it is appropriately directed to the anatomy of interest and so that it does not extend beyond the outer edges of an imaging detector. Collimation also helps to reduce scattering of radiographic energy. With CNT or other types of small x-ray sources in an array, collimation techniques present particular challenges. One set of problems relate to dimensional constraints. Because the spacing between such x-ray sources is typically small, it can be difficult to effectively bound the radiation energy emitted from any individual source. Crosstalk can occur, making it difficult to clearly define edges of the radiation field. Still other complexity relates to identifying the radiation field for imaging from each source. With conventional radiography sources, the problem is readily solved: a light source that is coupled to the radiography source can be used to outline or otherwise highlight a radiation field represented by visible light, by adjusting the collimator edges. However, it can be impractical or impossible to provide a corresponding dual-use arrangement using collimator openings provided for CNT and other types of distributed array sources.

Thus, it can be seen that although there can be advantages in using a distributed array of x-ray sources for tomography and other types of depth imaging, existing collimation strategies fall short of what is needed to more effectively collimate the emitted radiation and generate useful image projections and reconstructions.

SUMMARY

An object of the present disclosure is to address the need for improved collimation for imaging apparatus that use a distributed array of x-ray sources. Aspects of the present disclosure provide solutions that can not only provide collimation adapted to the special characteristics of the distributed array of x-ray sources, but can also take advantage of particular capabilities and features for systems that use such distributed arrays. Another aspect of this application is to address, in whole or in part, at least the foregoing and other deficiencies in the related art, while providing improved ways to collimate the field that x-ray source arrays radiate.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided a radiographic imaging apparatus comprising a radiation detector, a radiation source array having a plurality of radiation sources, a control processor configurable to individually energize each of the plurality of radiation sources in the radiation source array, a collimator member movable to be disposed at either a first position or a second position in a path of the radiation source array and having a plurality of apertures. The collimator member may be disposed at the first position, wherein the plurality of apertures define a first subset of the radiation sources in the array and define a radiation field on the radiation detector. The collimator member may be disposed at the second position, the plurality of apertures may define a second subset of the radiation sources in the array, different from the first subset by at least one member. The second subset of the radiation sources have may have a radiation field that is defined for the first subset of the radiation sources with the collimator member in the first position. A transport apparatus translates the collimator member between at least the first and second positions according to an instruction from the control processor.

BRIEF DESCRIPTION OF THE DRAWINGS

The foregoing and other objects, features, and advantages of the invention will be apparent from the following more particular description of exemplary embodiments of the invention, as illustrated in the accompanying drawings. The elements of the drawings are not necessarily to scale relative to each other.

FIGS. 2A, 2B, 2C, 2D, and 2E, 2F, 2G, and 2H are perspective views that show a radiation source assembly for radiographic imaging systems and/or methods that can implement both projection and tomosynthesis imaging according to embodiments of the present disclosure.

FIG. 6B is a bottom view showing a collimator plate assembly with apertures of different aspect ratios.

FIGS. 6C and 6D are bottom views that show an alternate collimator plate arrangement that is translated in a linear direction to position different sets of apertures over different subsets of the radiation source array.

DETAILED DESCRIPTION OF THE EMBODIMENTS

Figure 1:
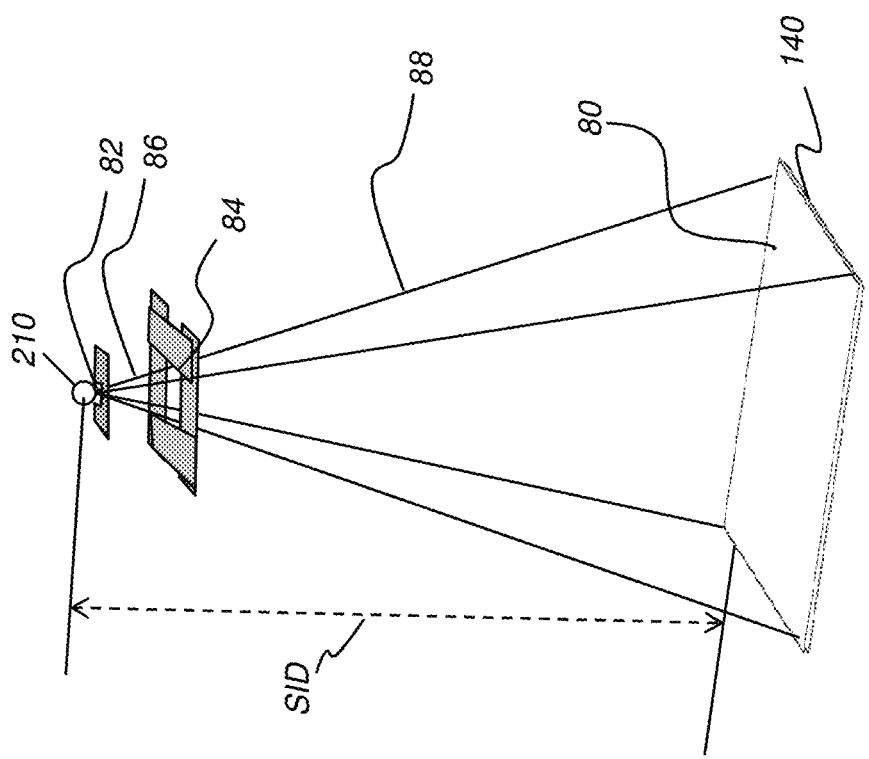
FIG. 1 is a schematic diagram that shows general geometric considerations and collimator components used to form a radiation field.

The following is a detailed description of the preferred embodiments, reference being made to the drawings in which the same reference numerals identify the same elements of structure in each of the several figures.

Where they are used herein, the terms "first", "second", and so on, do not necessarily denote any ordinal, sequential, or priority relation, but are simply used to more clearly distinguish one element or set of elements from another, unless specified otherwise.

In the context of the present disclosure, the terms "viewer", "operator", "viewing practitioner", "observer", and "user" are considered to be equivalent and refer to the viewing practitioner or other person who views and manipulates an x-ray image on a display monitor or other viewing apparatus.

As used herein, the term "energizable" relates to a device or set of components that perform an indicated function upon receiving power and, optionally, upon receiving an enabling signal.

The term "actuable" has its conventional meaning, relating to a device or component that is capable of effecting an action in response to a stimulus, such as in response to an electrical signal, for example.

The term "modality" refers to types of imaging. Modalities for an imaging system may be conventional x-ray radiography, fluoroscopy or pulsed radiography, tomosynthesis, tomography, ultrasound, MMR, or other types of imaging. The term "subject" refers to the patient who is being imaged and, in optical terms, can be considered equivalent to the "object" of the corresponding imaging system.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members. For a set S, a subset may comprise the complete set S. A "proper subset" of set S, however, is strictly contained in set S and excludes at least one member of set S. A "partition of a set" is a grouping of the set's elements into non-empty subsets so that every element is included in one and only one of the subsets. Two sets are "disjoint" when they have no element in common.

The terms "image" and "image data" can be used interchangeably in the context of the present disclosure. An image that is captured by an imaging apparatus may be processed, displayed, transmitted, or stored as image data, or a combination thereof.

In the context of the present disclosure, the term "depth image" refers to a reconstructed image that represents depth image data obtained from processing multiple 2-D images or projection images of the subject, taken from different angles. Depth images can be obtained by tomosynthesis, which does not typically provide full 3-D imaging, or from computed tomography (CT) that provides more complete depth image data and is considered to provide full 3-D imaging. The noun "projection" may be used to mean "projection image", referring to one of the 2-D images that is captured and used to reconstruct a depth image.

In the context of the present disclosure, the term "aspect ratio" has its conventional meaning as related to two-dimensional polygons and other shapes and generally relates height to width in 2-D space. Thus, for example, two squares of different size exhibit the same aspect ratio. Two rectangles may or may not have the same aspect ratio. It should also be noted that a square is considered a special case of rectangular shape with equal sides. Aspect ratios are considered to differ from each other if the ratio between the two varies by more than about 10%.

Exemplary embodiments can address the collimation needs of an array of x-ray sources in any of a number of embodiments, including arrangements that use only distributed x-ray sources, or hybrid arrangements that may include both a conventional radiographic projection x-ray source and an array of CNT or other smaller sources. Embodiments of the present disclosure can be used with an array of x-ray sources that are arranged in a prescribed shape such as a circle, or which may be arranged about a central standard radiographic projection x-ray source that provides standard radiographic projection x-ray imaging. Exemplary embodiments can provide a translatable or rotatable collimator that simultaneously collimates each of a plurality of sources in an array or collimates all of the sources in an array while allowing the selection of one or more collimation fields of given shape and dimension. Exemplary embodiments can serve various capture geometries for the plurality of distributed sources and/or a central standard radiographic projection x-ray source.

The simplified schematic view of FIG. 1 shows some of the geometric considerations and relationships that relate to x-ray collimation for a single x-ray source 210 in general and establish definitions of terms used herein. X-ray source 210 is idealized as a point source, to a first approximation. Radiant energy from source 210 is directed along a radiation path that extends through and is initially formed by a first aperture 82 that is typically very close to source 210. Alternatively, the first aperture 82 may not be used. The radiant energy then continues along the radiation path 86 through a second aperture 84 along a radiation path 88 that shapes the radiant energy as an x-ray field 80 on a detector 140. The shape and dimensions of the radiation paths 86, 88, and the aspect ratio of x-ray field 80 are determined by geometric constraints such as the size and location of apertures 82, 84, relative to a location of the source 210, to each other, and source-to-image distance (SID). The shape of X-ray field 80 is typically bounded to fit the dimensions of detector 140 but may be smaller and a different shape, depending on the subject being imaged. It must be noted that FIG. 1 shows geometric relationships for a single source 210; embodiments described herein may have multiple x-ray sources 210, each having collimation along its radiation path in a similar manner to that shown in FIG. 1.

Figure 2A:
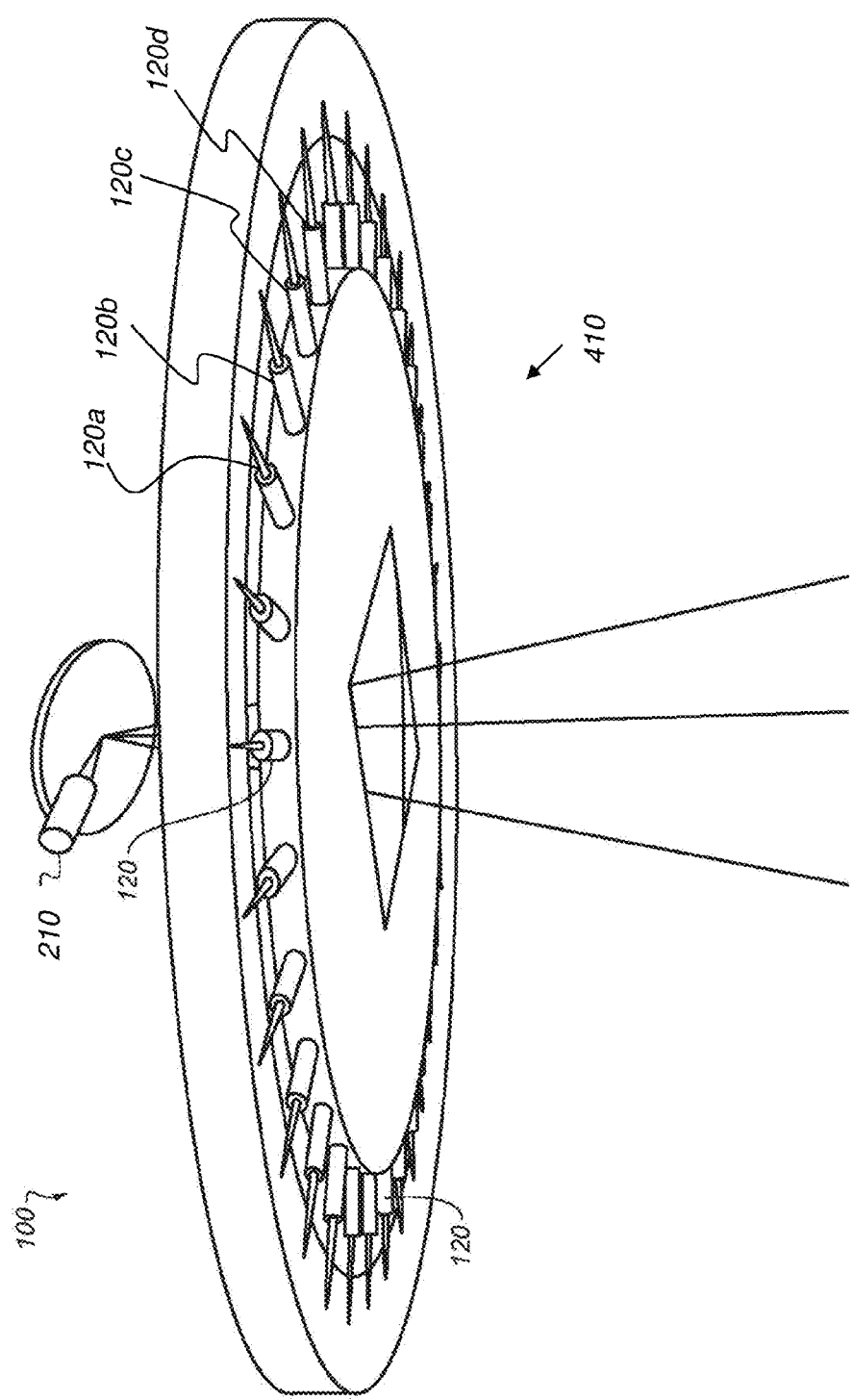
Figure 2B:
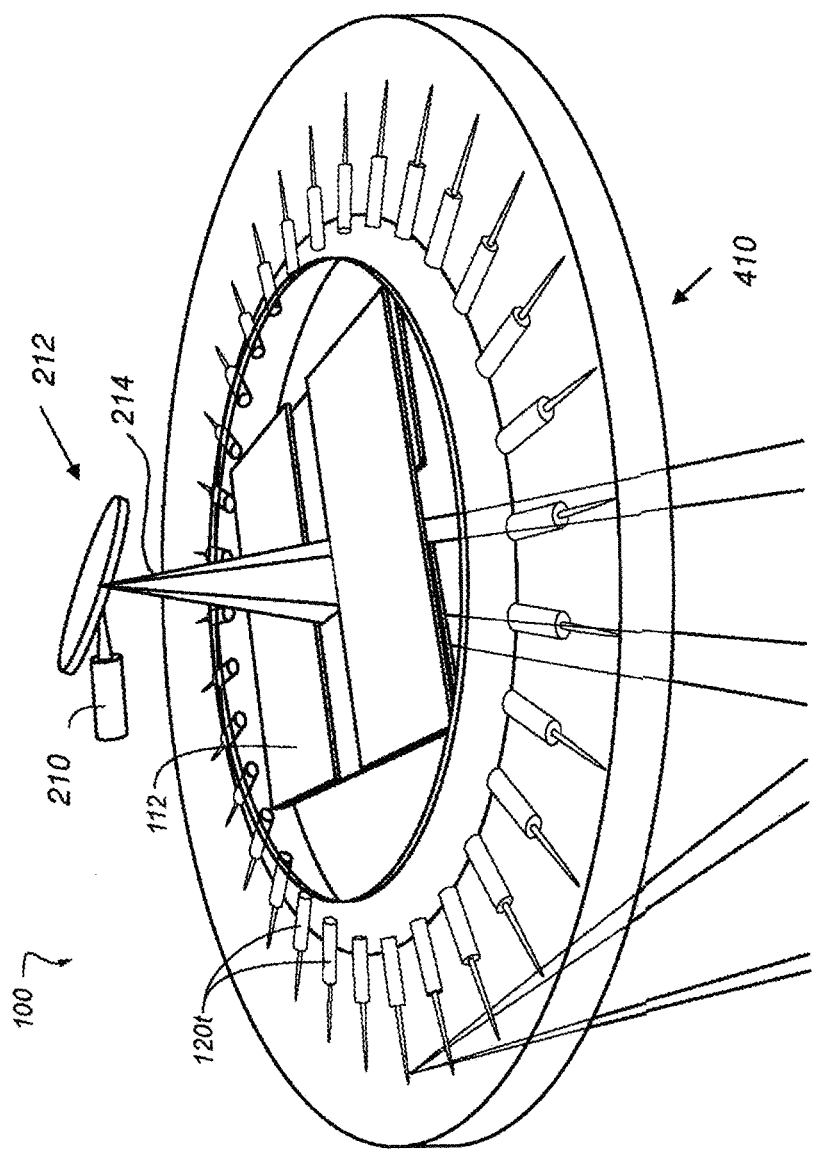

FIGS. 2A-2B show perspective views of a design arrangement of a portion of a radiation source assembly 100 that serves as a type of x-ray head for radiographic imaging systems and apparatuses according to one exemplary embodiment. Radiation source assembly 100 has a central radiography radiation source 210 with an x-ray generator 212 that generates sufficient energy for conventional radiographic imaging. In an array of radiation sources 410, additional peripheral radiation sources 120, 120a, 120b, 120c, 120t, such as CNT x-ray sources, may be arranged to lie in the same plane and may be distributed in a patterned arrangement about radiation source 210 to provide tomosynthesis imaging without requiring movement of a radiation source. A blade collimator 112 forms, or shapes, or defines, the radiation field 214 emitted by the radiation source 210 toward a radiation detector (not shown in FIGS. 2A, 2B). Within the distributed array 410 of sources 120, a source 120 can have adjacent or neighboring sources, using the conventional understanding of adjacent features. In the example of FIG. 2A, source 120b has two adjacent or neighboring sources, sources 120a and 120c. Source 120d is adjacent to source 120c.

Figure 2C:
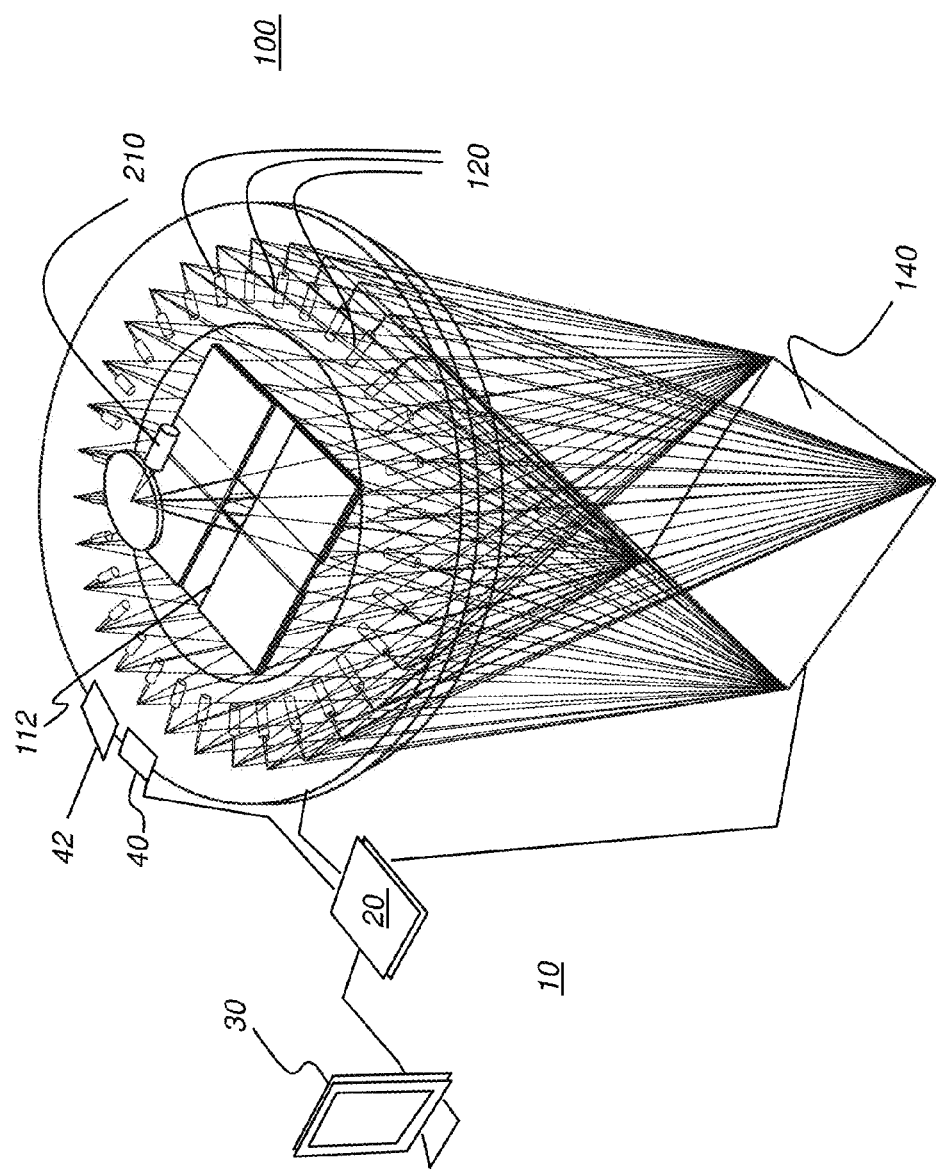

FIG. 2C shows a perspective view of an imaging apparatus 10 that directs radiation to detector 140 from source 210 or from any subset of sources 120 in order to provide both projection and tomosynthesis imaging according to embodiments of the application. A processor 20 controls the energization sequence for each of the distributed sources 120 and for the central source 210. Processor 20 also obtains the image data from detector 140 and processes the obtained images to generate either radiography or tomosynthesis images for display on a display 30. The generated images can also be stored, such as at a local memory or other data storage apparatus and transmitted, such as to a remote host processor, memory, or data storage location.

FIG. 2C shows the radiation field of each of the sources, with radiation paths superimposed on each other, for directing radiation to detector 140. FIG. 2D shows a central radiation field 150 on detector 140 for radiation source 210. The shape, aspect ratio, and dimensions of radiation field 150 are controlled by collimator 112. FIG. 2E shows a radiation field 152 for one of distributed sources 120.

Figure 2F:
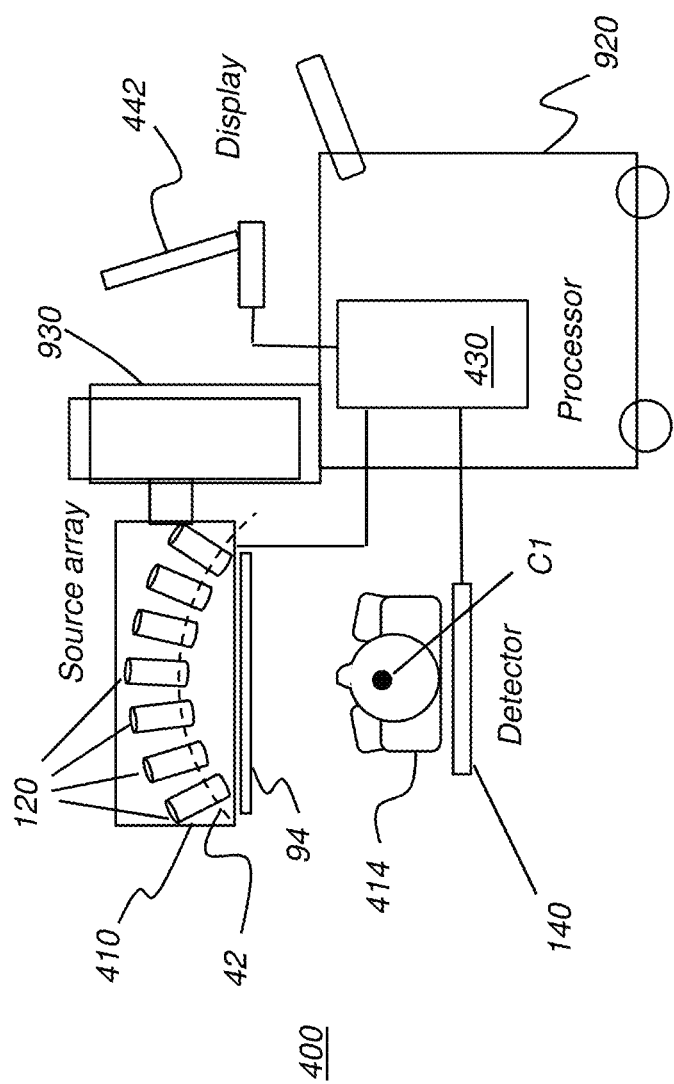

The schematic block diagram of FIG. 2F shows a portable radiography apparatus 400 that has an x-ray source array 410 but does not also include a standard x-ray source for general radiography. A collimator member 94 is provided, shown as a single plate or other unit, as described in more detail subsequently. Multiple x-ray sources 120 in source array 410 are shown configured in a curved arrangement, each directed toward a focal point C1 at the patient 414. A transport assembly 930 provides a variable-height boom for raising and lowering source array 410 into position. Portable radiography apparatus 400 has a processor 430 for image acquisition, system control, and display and operator interface functions using a display 442. A transport assembly 920 provides a cart for moving portable radiography apparatus 400 between sites.

Figure 2G:
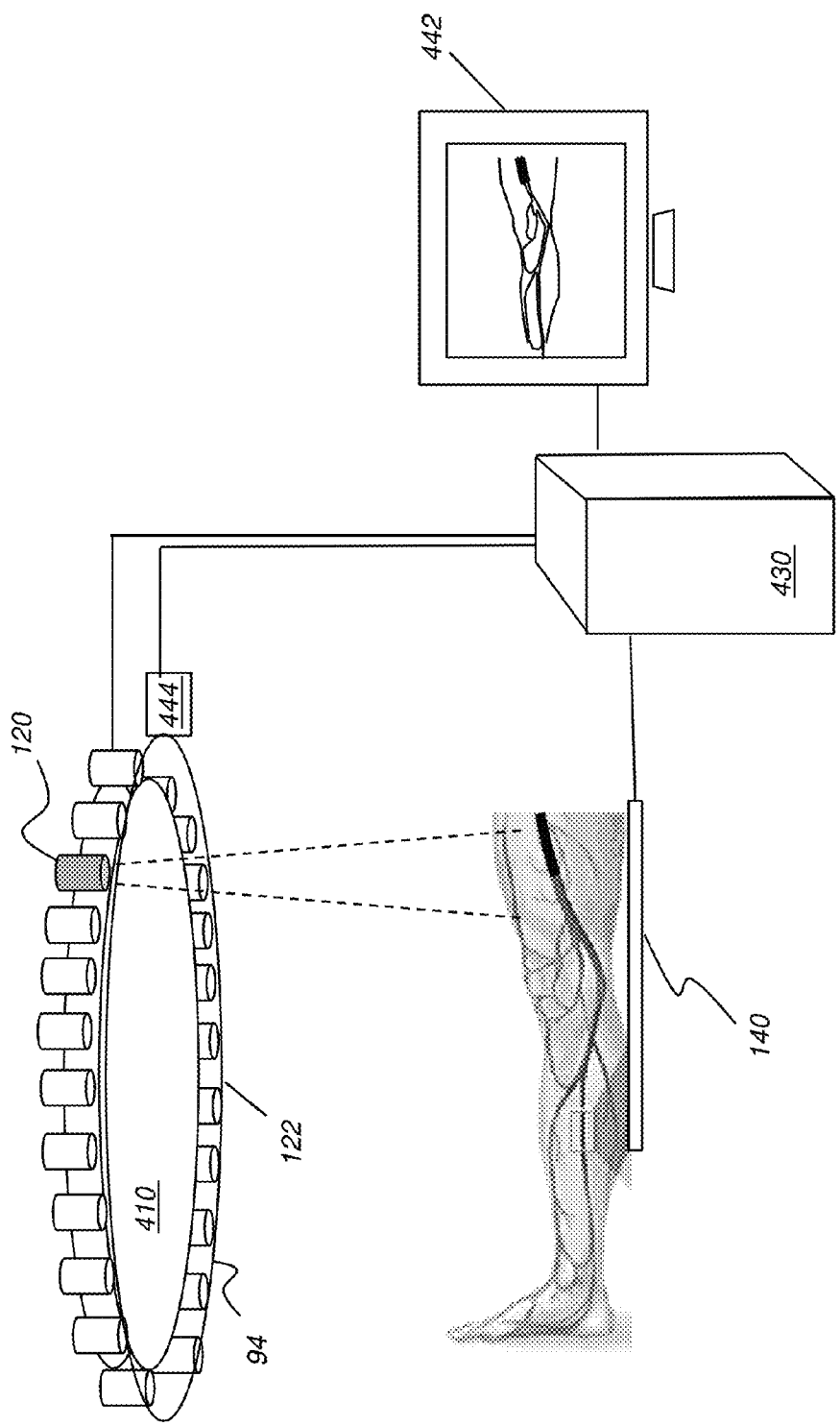

The schematic diagram of FIG. 2G shows x-ray source array 410 with sources 120 arranged around the circumference of a circular ring. Collimator member 94, such as a collimator plate assembly 122 as described in more detail subsequently, provides an arrangement of apertures for blocking some sources and shaping the output x-ray energy from each of one or more apertured sources 120. In addition to image acquisition from detector 140, processor 430 controls both the actuation sequence for energizing each of sources 120 and an actuator 444 that rotates or otherwise translates collimator member 94 into position for each acquired image used in tomosynthesis. Collimator member 94 can be held in one position, so that it apertures only those sources 120 that are used for a tomosynthesis sequence. According to an alternate embodiment of the present disclosure, collimator member 94 is rotated to each of a number of rotational positions about the periphery of circular array 410 in order to provide the needed radiation field for each source 120.

Figure 2H:
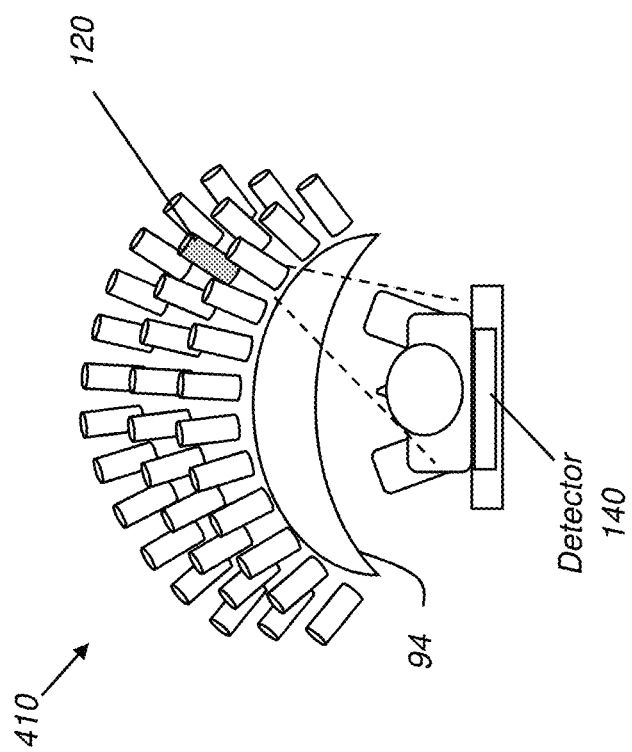

The schematic diagram of FIG. 2H shows x-ray source array 410 with sources 120 arranged about a curved surface. Collimator member 94 can be a single unit that is translated to different positions or can be a composite assembly having two or more plates or other apertured surfaces that cooperate to provide the needed radiation field.

For certain exemplary embodiments, such as the FIG. 2H arrangement, the distributed source 120 arrays are not co-planar and can implement a different SID for an imaging event or examination. For example, portions of the distributed source 120 arrays can be selectively co-planar, for example, two sides at different depths, three of four sides at different planes. Further, the (vertical, horizontal) distance between the arrays can be the same or different (e.g., increasing). Alternatively, adjacent or opposite pairs of source 120 arrays can have equal SIDs or be co-planar. Such a variation in arrangement can allow for a fixed x-ray source arrangement to implement a greater range of subject distances.

As FIGS. 2C and 2E in particular suggest, collimation is a particular challenge where there are multiple distributed radiation sources. Embodiments of the present disclosure address the problem of collimation for an array of radiation sources and provide solutions that allow more effective use of the distributed radiation sources for tomosynthesis imaging.

Figure 3:
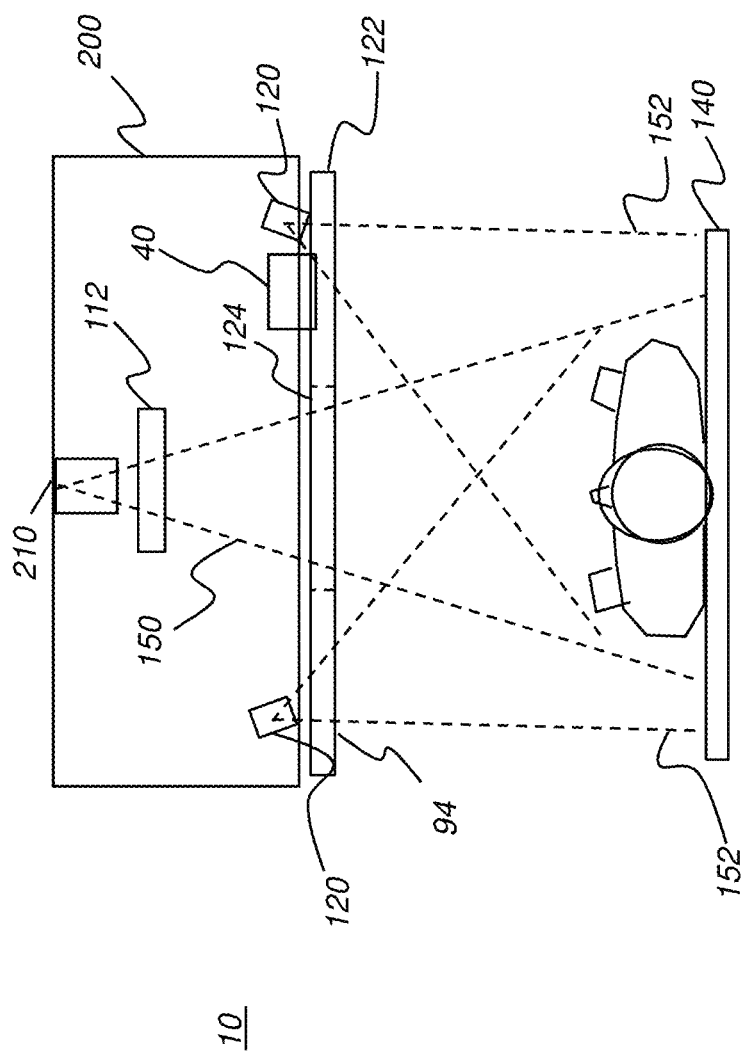
FIG. 3 is a side view of the radiation source assembly having different source types.

FIG. 3 shows a side view of imaging apparatus 10 with radiation source assembly 200 having a distributed source collimator as collimator member 94, collimator plate assembly 122. Radiation fields 150, 152 are outlined for their respective source 210 and for two of the sources 120. As FIG. 3 shows, the geometry of source 210 and apertures in collimator 94 define the radiation field 152 on detector 140.

Figure 4:
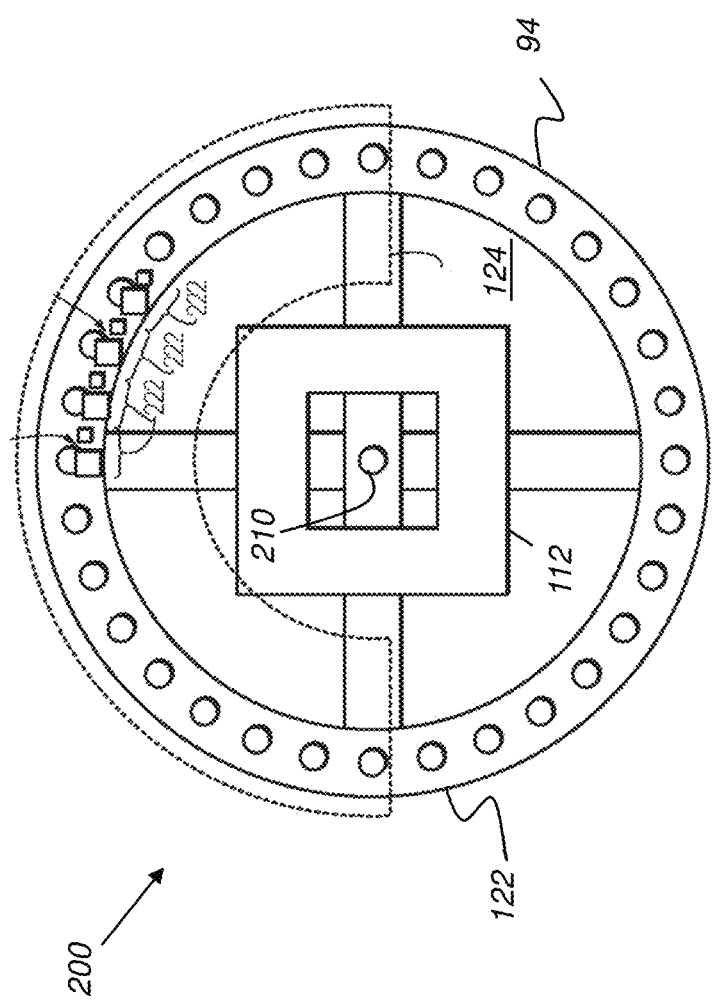
FIG. 4 is a bottom view of a collimator plate assembly.

FIG. 4 shows a bottom view of collimator plate assembly 122 that serves as collimator member 94 for distributed sources 120 in radiation source assembly 200. Collimator plate assembly 122 has a number of peripheral collimation apertures 222 for shaping the radiation field of any of the corresponding distributed sources 120. Collimator plate assembly 122 is formed as a ring having a central opening 124 that lies in the path of the first radiation field 150 (FIG. 3) from radiography radiation source 210.

Where multiple sources 120 are provided in an array, only a single source 120 is energized at a time and typically only a subset portion of the sources 120 may be used for any sequence of projection images; the remaining sources 120 are temporarily de-energized and blocked by the collimator. Collimator plate assembly 122 can be configured to allow transmission and shaping of energy from each of the distributed sources 120 or, alternately, to provide apertures for only a partial subset of the distributed sources 120 at one time. The capability to allow collimation for members of a partial subset of the available sources 120 at a time can be particularly useful for tomosynthesis imaging, allowing radiation at different angles without adjustment of the collimator or movement of the radiation sources themselves between images. Collimator plate assembly 122 can be rotatable, so that the subset of sources 120 that can be collimated, that is, the subset of apertured sources 120, can be changed with successive exposures.

Figure 5A:
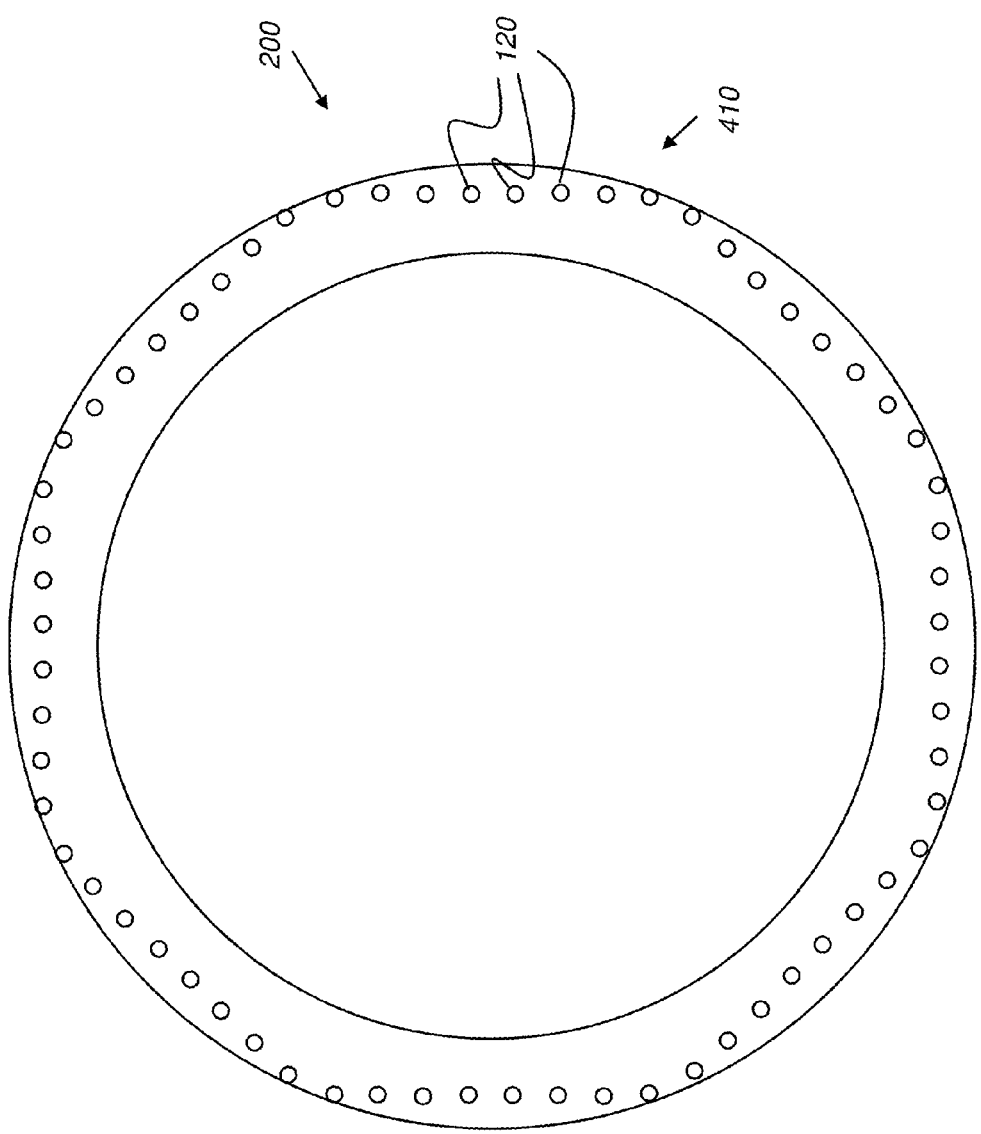
FIG. 5A is a bottom view of the radiation source assembly showing an arrangement of distributed radiation sources.

The bottom views of FIGS. 5A-5D show an arrangement of sources 120 and corresponding peripheral collimation apertures 222 on collimator plate assembly 122. FIG. 5A shows the arrangement of distributed sources 120 in an octagonal pattern within radiation source assembly 200, as these would be arranged behind collimator plate assembly 122 shown in FIG. 5B.

Figure 5B:
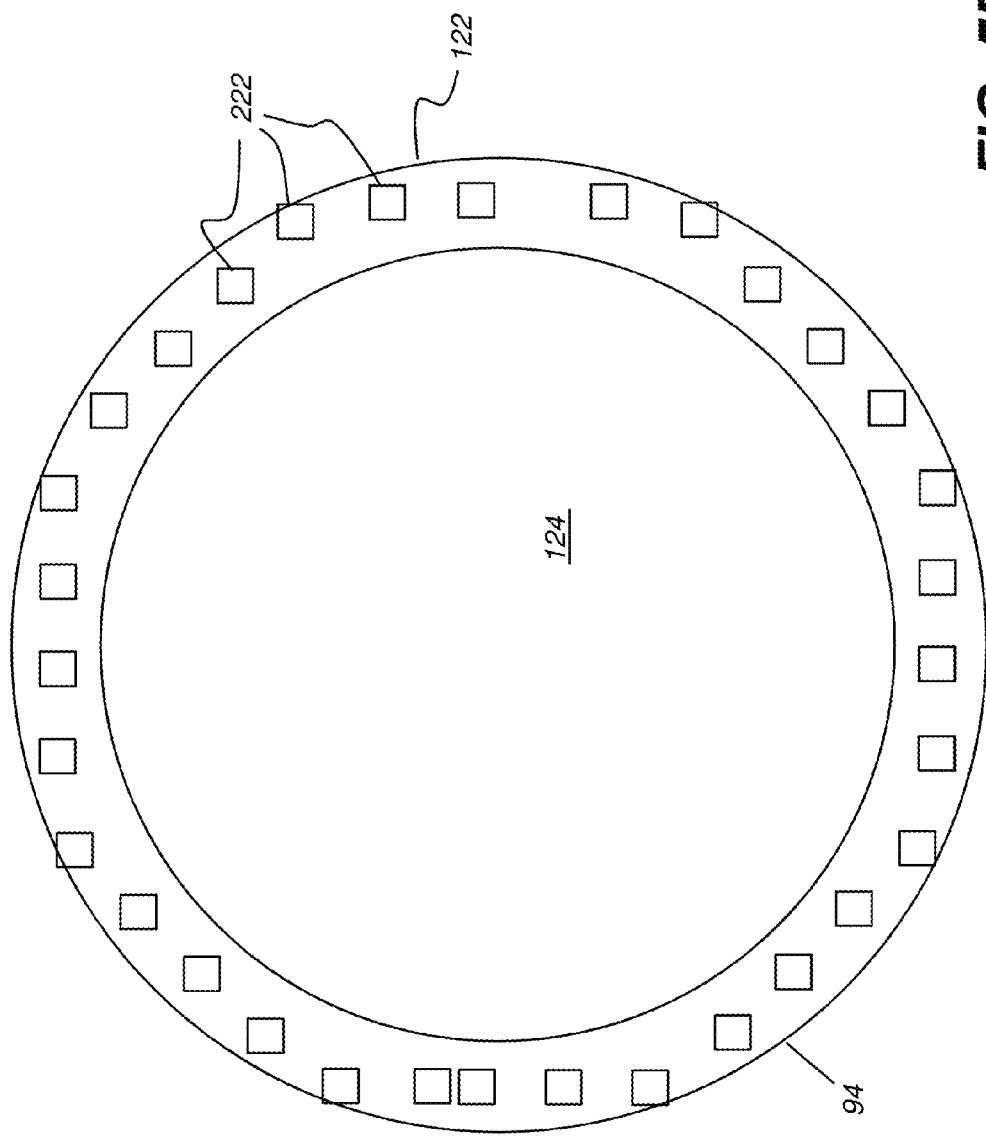
FIG. 5B is a bottom view of a collimator plate assembly.
Figure 5C:
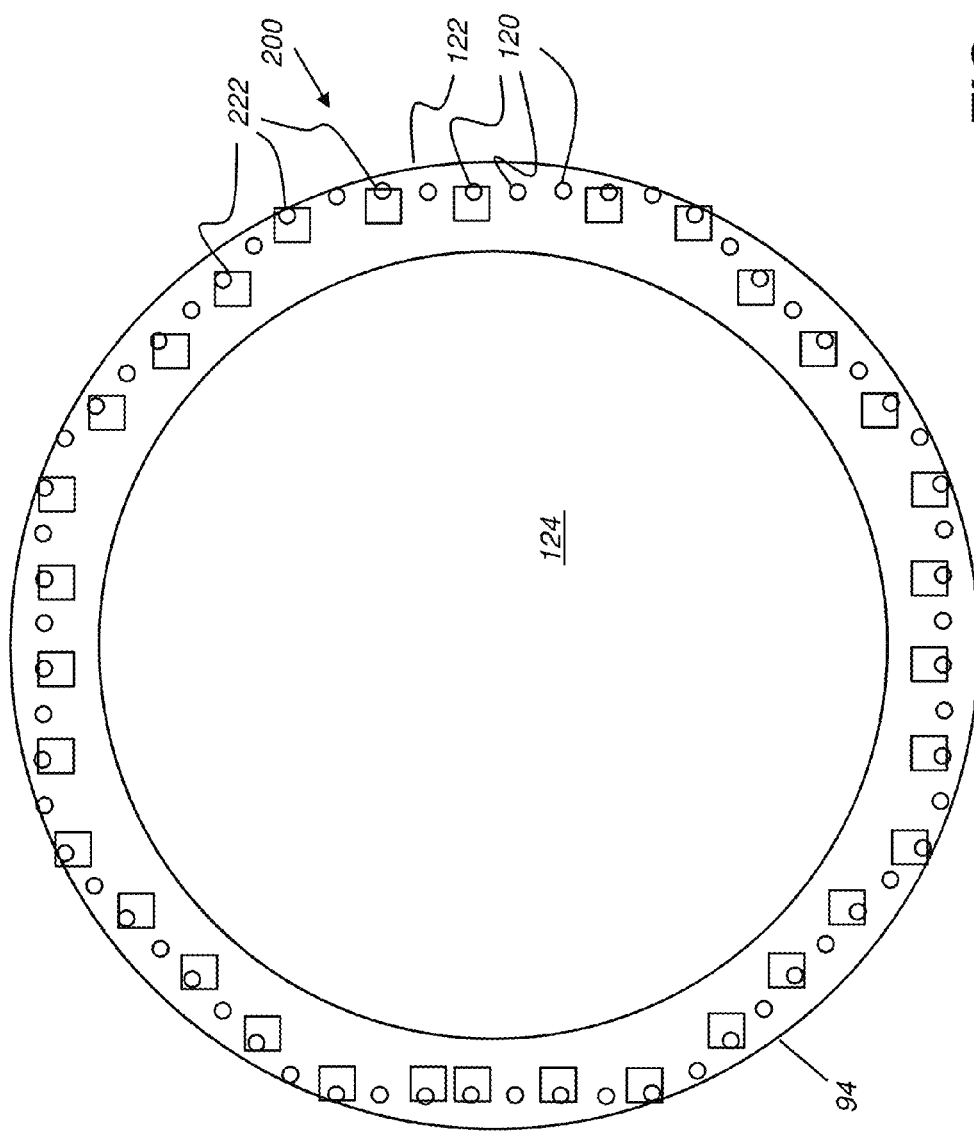
FIG. 5C is a bottom view that shows the collimator plate assembly in one position with respect to the distributed radiation sources.
Figure 5D:
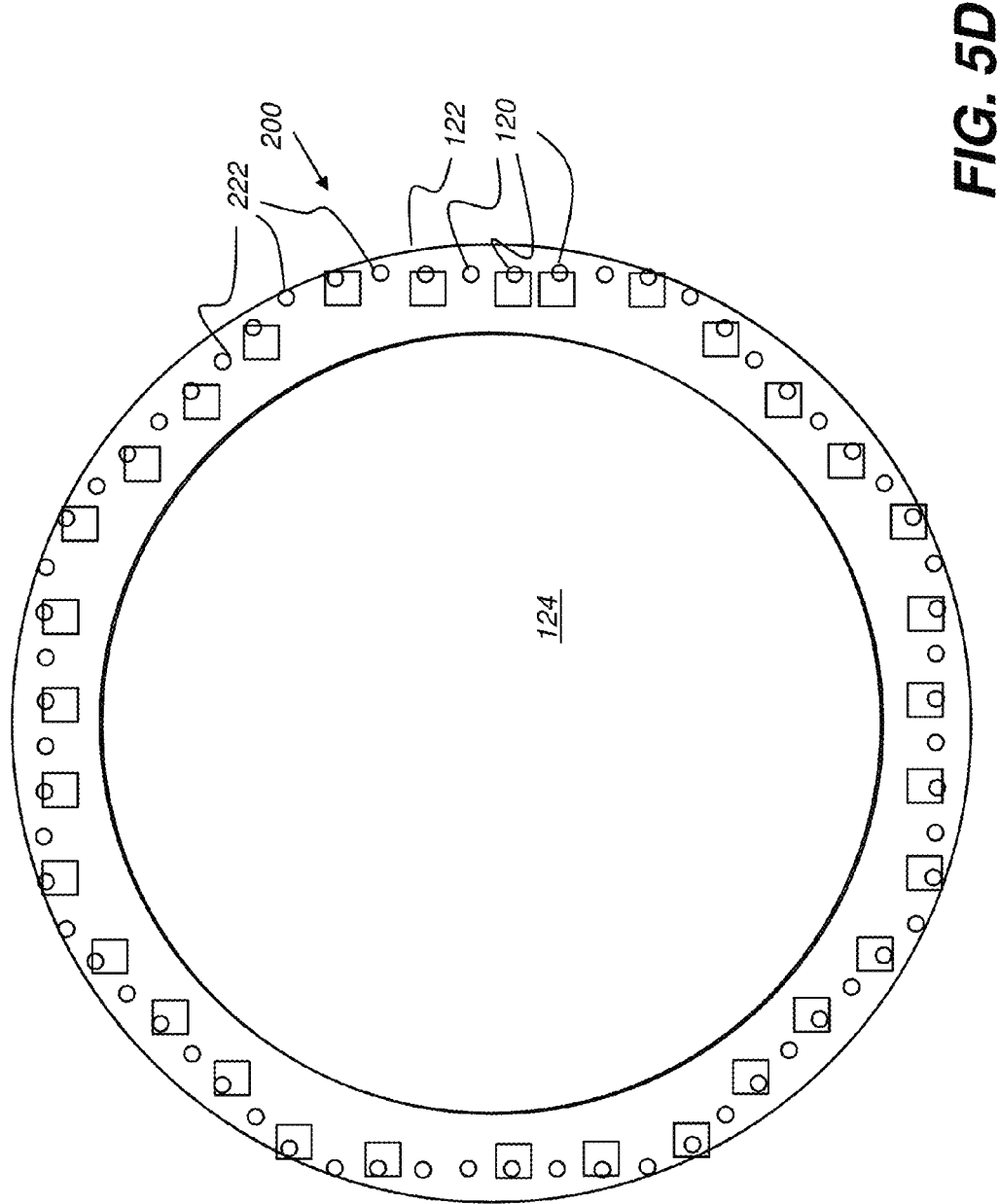
FIG. 5D is a bottom view that shows the collimator plate assembly in an alternate position with respect to the distributed radiation sources.

FIG. 5C shows collimator plate assembly 122 in a first position for providing radiation fields from a first apertured subset of the distributed sources 120. The first subset uses half of the sources 120; the remaining half of the sources 120 are blocked by collimator member 94 and would be temporarily de-energized. FIG. 5D shows collimator plate assembly 122 in a second position, rotated 180 degrees from the first position of FIG. 5C. In the FIG. 5D position, the apertured subset of sources 120 that can be collimated includes all of the sources 120 that were blocked and de-energized and not used in the first position of FIG. 5C and none of the sources that were apertured in the FIG. 5C position. Thus, the subset of apertured or collimated sources 120 in the FIG. 5C position is mutually exclusive from the subset collimated in the FIG. 5D position. The two subsets are disjoint and complementary, so that each source 120 in radiation source assembly 200 is collimated in one and only one of the two rotational positions shown in FIGS. 5C and 5D. The use of a circular collimator plate assembly 122 that is rotatable between positions is one aspect of the present disclosure; other collimator geometries and types of collimator transport devices can alternately be used for providing and translating an arrangement of apertures at different positions relative to the radiation source assembly 200, as described in more detail subsequently. In addition, multiple collimation devices can cooperate to provide the functions of circular plate assembly 122.

The arrangement of sources 120 used in the particular example of FIGS. 5A-5D utilizes a generally octagonal pattern that allows collimator plate assembly 122 rotation to different angular positions for radiation from a different subset of sources 120. The number of usable rotational positions varies, depending on the overall aspect ratio of the detector that is used. For a rectangular detector, collimator plate assembly 122 has two rotational positions, as described with reference to FIGS. 5C and 5D, each position providing apertures 222 for a subset that includes half of the sources 120 in radiation source assembly 200. As has been described, each of the two rotational positions provides apertures 222 for a different subset of sources 120, with the two subsets complementary or mutually exclusive, so that each source 120 is blocked when the collimator plate assembly 122 is in one of the two positions and is apertured so that it can be energized in the other position.

Continuing with the example of FIGS. 5A-5D, for a square detector, rotation of collimator plate assembly 122 to each of four different angular positions is suitable, allowing the selection of more than two different subsets of the sources 120 according to collimator plate assembly 122 rotational position.

With respect to imaging apparatus 10 in FIG. 2C, processor 20 can energize each of the distributed sources 120 independently, corresponding to the rotational position of collimator plate assembly 122. Collimator plate assembly 122 can be manually rotated into position or may be rotated by an actuator 40. One or more sensors 42 can be used to report angular orientation of collimator plate assembly 122, such as using Hall effect sensors or other sensor types, well known to those skilled in the position sensing arts.

With respect to the general description given in FIG. 1, the near-source aperture 82 for each source 120 can be in a fixed position relative to source 120 and with far aperture 84 having its position adjustable, such as by rotation or translation. As FIG. 1 showed, far aperture 84 and the SID have pronounced impact on the shape and dimensions of the collimated radiation field.

Collimator plate assembly 122 can be configured to be rotated or otherwise translated to specific spatial or angular positions in order to provide the needed collimation for forming a radiation field of corresponding shape. For example, FIG. 5B shows collimation apertures 222 having a generally rectangular shape and thus well-suited to forming a radiation field that corresponds to the edges of a rectangular imaging detector. Collimator plate assembly 122 can be rotated to either of two angular positions, 180 degrees apart from each other, to form a rectangular field having an aspect ratio corresponding to apertures 222. In a first angular position, one half of sources 120 can be energized; these are the sources that correspond to apertures at the first angular position. At a second angular position, rotated 180 degrees from the first position, the other half of sources 120 can be energized, providing a radiation field of the same aspect ratio.

It can be observed that the arrangement of sources 120 that are shown in FIG. 5A can alternately be used for forming a radiation field that has a square aspect ratio, such as for a square detector. Apertures 222 would be square, rather than the rectangular shape that is shown in FIGS. 5B-5D. Collimator plate 122 can then be rotated to any of 4 rotational positions, due to the symmetry of the radiation field shape.

Figure 6A:
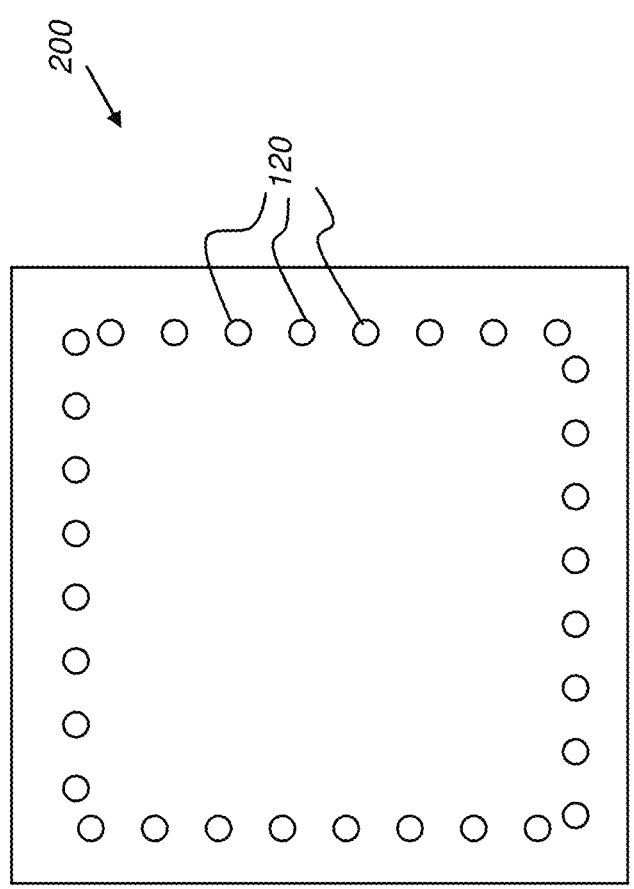
FIG. 6A is a bottom view that shows a radiation source assembly in a substantially square arrangement.

According to an embodiment of the present disclosure, array of sources 120 can be used with rotatable collimator plate assembly 122 to form radiation fields of various shapes and aspect ratios depending on the dimensions of apertures 222, rotation angle of collimator plate assembly 122, and the arrangement of corresponding sources 120 that are energized in the energization sequence. Thus, for example, with respect to FIG. 6A, radiation source assembly 200 has a generally square shape with sources 120 distributed along the sides of the square. Collimator plate assembly 122 in FIG. 6B has apertures 222a and 222b of more than one aspect ratio. One set of apertures 222a is square; the other apertures 222b are rectangular. By rotating collimator plate assembly 122 to different positions and energizing the corresponding apertured sources 120 for the given radiation field shape, the sources 120 can be used in sequence to provide the needed radiation field shape.

Figure 6E:
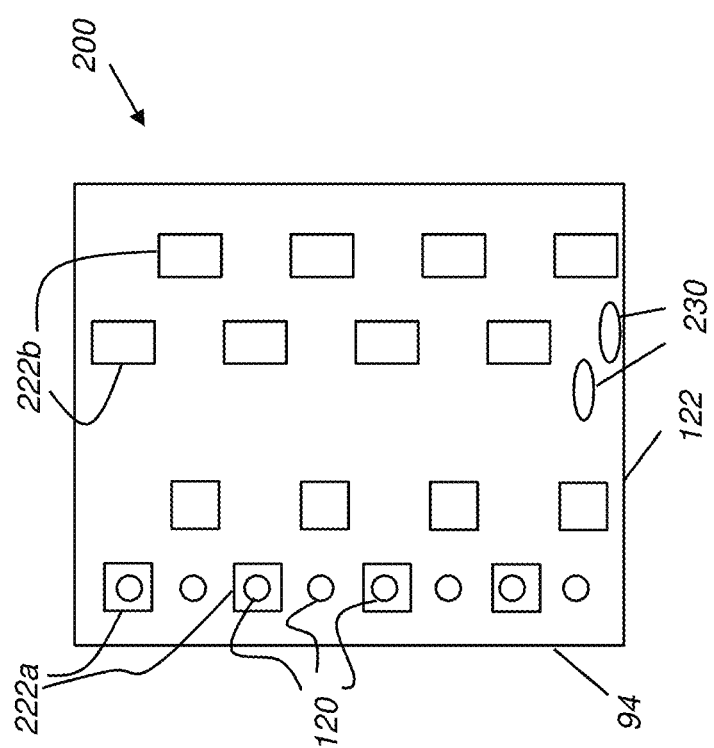
FIG. 6E is a bottom view that shows a collimator plate having paired sets of apertures of different aspect ratios.

FIGS. 6C and 6D show another alternate arrangement in which collimator plate assembly 122 is translatable back and forth in a single direction, along the direction indicated by a line L1. In this example, radiation source assembly 200 is a linear array of sources 120. A set of square apertures 222a are arranged so that a subset of half of the apertures align to sources 120 with plate assembly 122 in a first position (FIG. 6C) and the subset with the other half of the apertures align to sources 120 with plate assembly 122 in a second position (FIG. 6D). FIG. 6E shows another arrangement, in which two different types of apertures are provided, a set of square apertures 222a in two subsets to be positioned in similar fashion to those shown in FIGS. 6C and 6D, and a set of rectangular apertures 222b, also used in a similar manner.

Figure 6G:
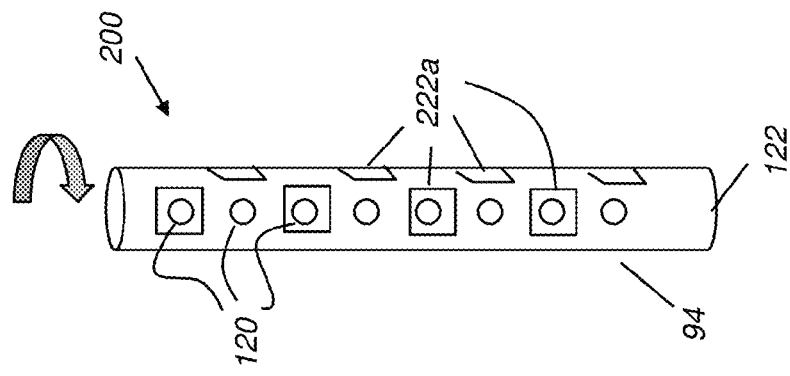
FIG. 6G is a view of a collimator that is curved and translated by rotating about a linear distributed source array.
Figure 6F:
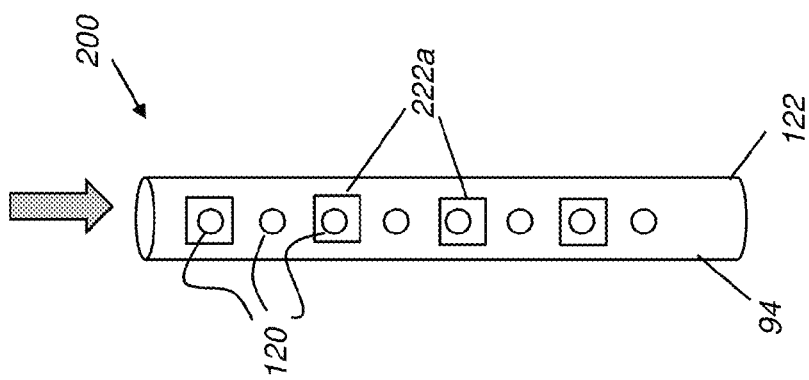
FIG. 6F is a view of a collimator that is curved and translated linearly along a linear distributed source array.

FIGS. 6F and 6G show another alternate embodiment in which collimator plate assembly 122 has a generally curved or tubular shape, with apertures 222a arranged for x-ray sources 120 in a linear radiation source assembly 200. In the arrangement of FIG. 6F, collimator plate assembly 122 is moved in linear fashion to shift apertures 222a between subsets of x-ray sources 120. In the arrangement of FIG. 6G, collimator plate assembly 122 is rotated about the linear array to shift apertures 222a between subsets of x-ray sources 120.

Collimator plate assembly 122 can be formed from a pair of metal plates, spaced apart from each other to form apertures 82 and 84 (FIG. 1) and with apertures 84 sized and positioned for suitable beam shaping. Apertures are aligned with source 120 positions based on the needed beam profile and angle. Near-source apertures 82 can be in fixed positions, with only the far apertures 84 adjustable.

Figure 6H:
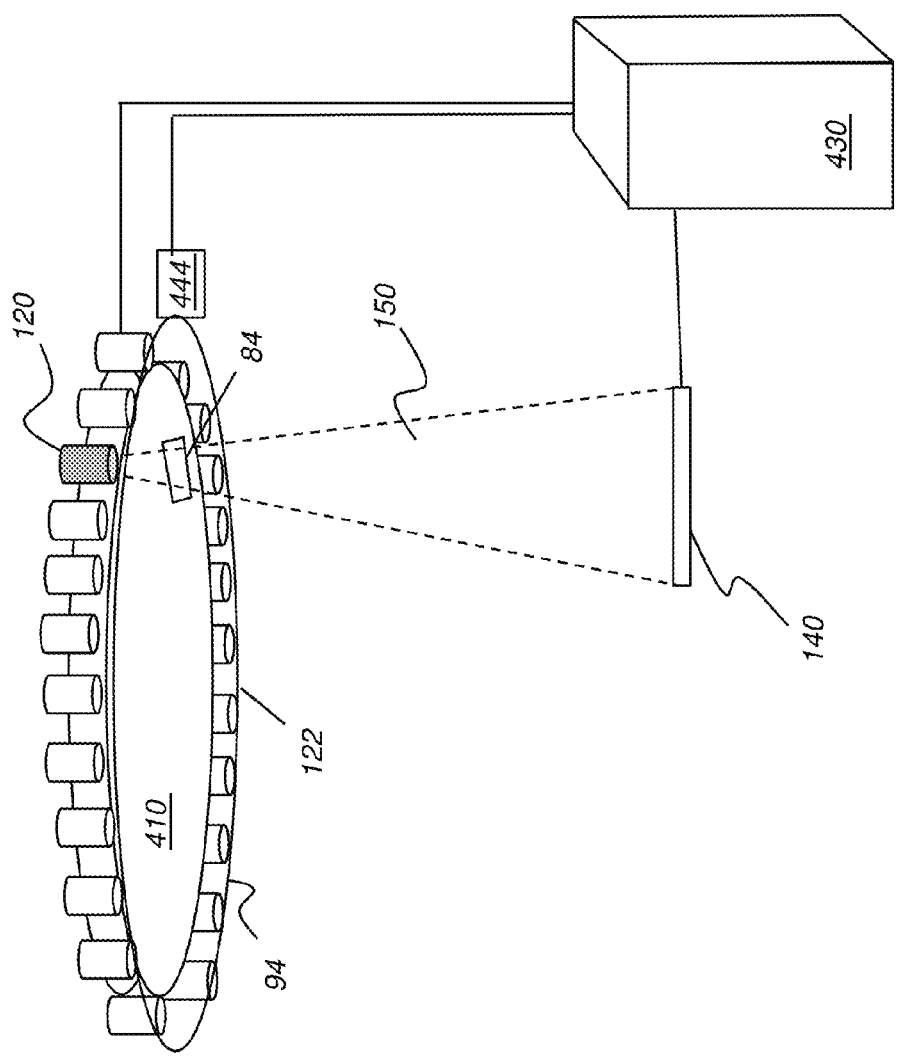
FIGS. 6H and 6I show an alternate embodiment of the present disclosure in which the height of the collimator is varied between two or more vertical positions in order to change the dimensions of the radiation field.
Figure 6I:
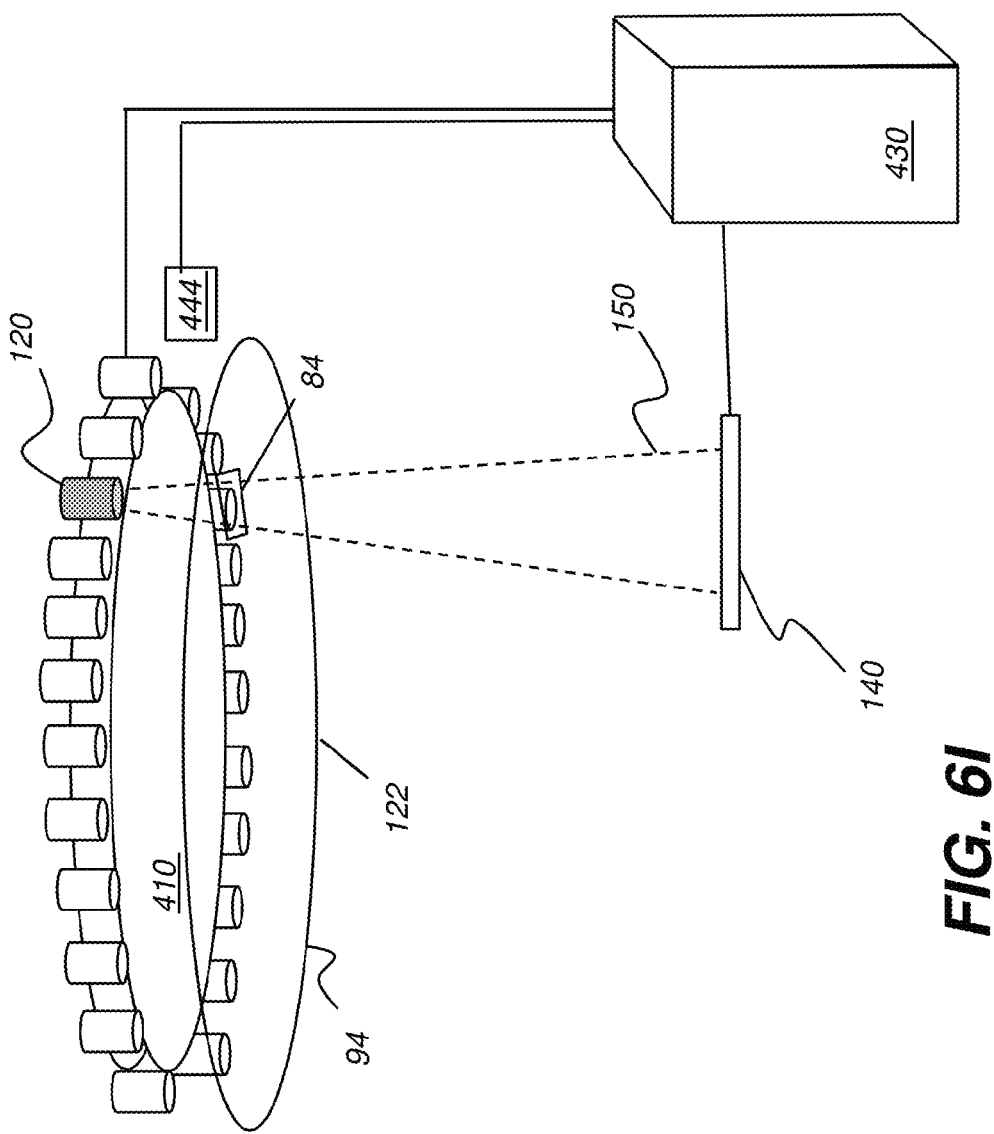

FIGS. 6H and 6I show an alternate embodiment of the present disclosure in which the height of collimator plate assembly 122, that is, its distance from detector 140 along the radiation path, can be varied between two or more vertical positions in order to change the dimensions of the radiation field 150. At the higher position of FIG. 6H, with aperture 84 at a first position, radiation field 150 extends the length of detector 140. With collimator plate assembly 122 and, consequently, aperture 84 at the lower position, exaggerated in FIG. 6I, radiation field 150 is slightly smaller than the detector 140 in length.

Figure 7A:
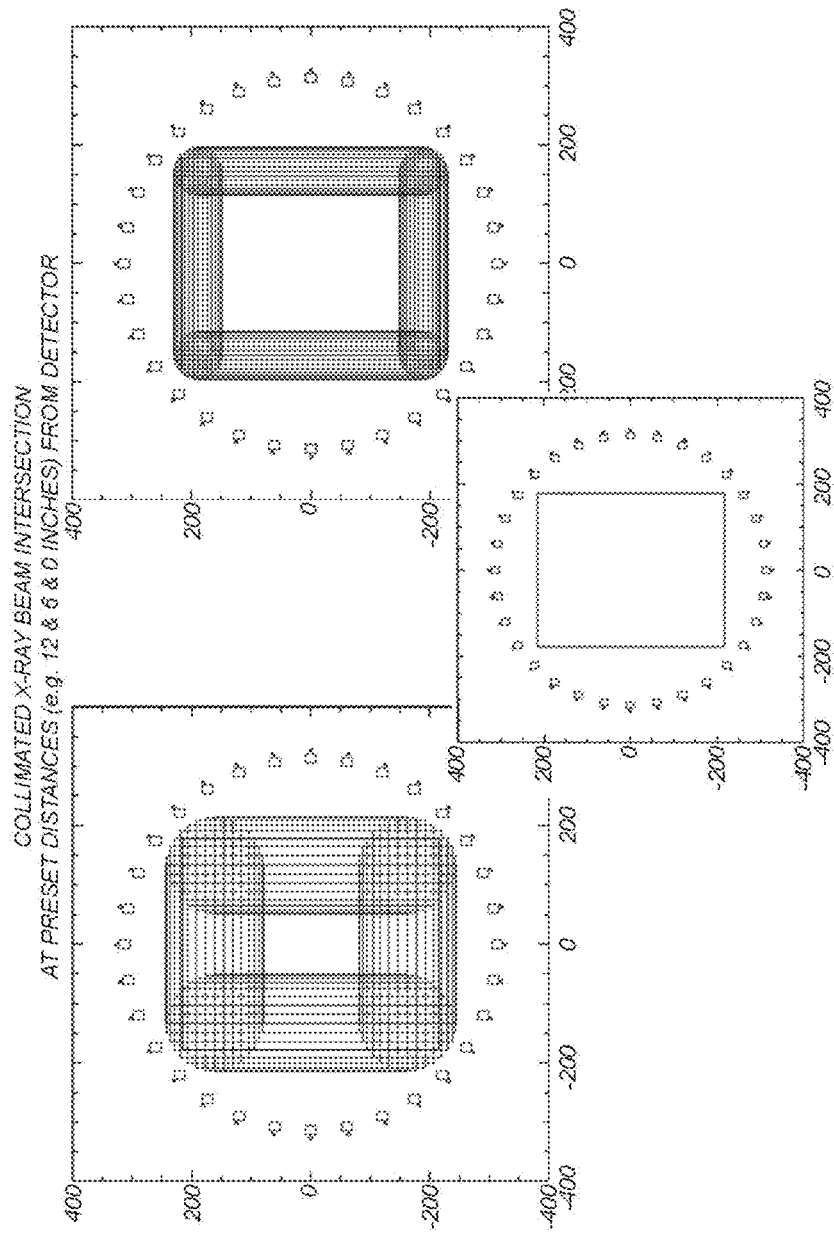
FIG. 7A is a diagram that shows the intersection of the collimated fields with planes at different heights.

FIG. 7A is a diagram that shows the intersection of the collimated fields with planes at different heights (e.g., from a detector). Of interest for image acquisition is the extent of the field at the detector.

Figure 7B:
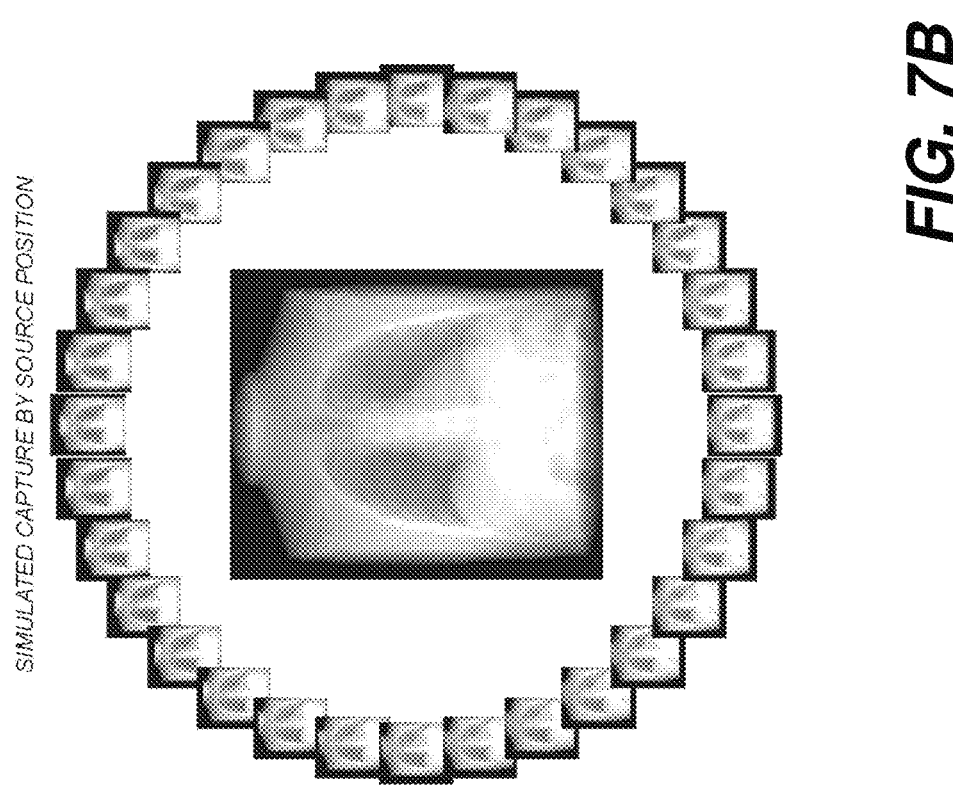
FIG. 7B is a diagram that shows simulations of exemplary projection x-rays from each source position according to another embodiment of the application.

FIG. 7B is a diagram that shows simulations of images acquired using radiation directed from each source angle position.

Figure 8:
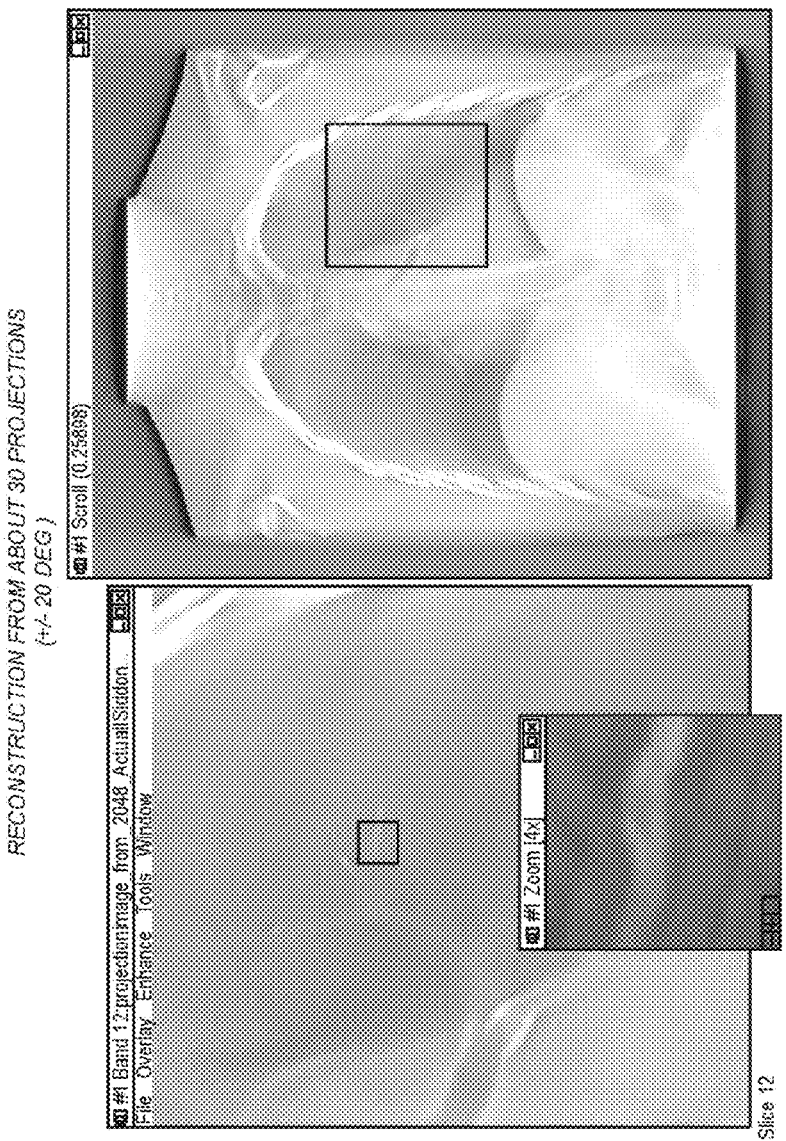
FIG. 8 is a diagram that shows a simulation of an exemplary reconstruction from the exemplary projection x-rays that can provide a tomosynthesis capability according to embodiments of the application.

FIG. 8 is a diagram that shows simulation of an exemplary reconstructed slice from processing images acquired using the exemplary projection x-rays.

In one embodiment of the present disclosure, the arranged or distributed low power sources can be an array of carbon-nanotube cathode x-ray sources. In one embodiment, a plurality or all of the electron beams emitted by the carbon nanotube cathode x-ray sources arranged on the periphery of radiation source assembly 200, are directed at a single, shared anode. This anode embodiment can be a disc with a hole in the center. For example, one anode embodiment can have a beveled edge so the electron beam can impinge the anode embodiment at the correct angle for x-ray emission. Further, the anode embodiment (e.g., disk) can rotate so the points where the electron beams hit can trace out line segments that can distribute the energy over a larger surface area of the anode to reduce damage (e.g., overheating, melting).

Certain exemplary embodiments shown in the figures described previously also show a central x-ray source that uses a conventional movable-blade collimator, as in FIG.

2B. This central x-ray source(s) can be used to capture traditional x-ray images, also termed general radiation or "gen rad" images. Further, the central x-ray source can also be used as one of the distributed sources to capture one or more of the multiple projection x-ray images that are processed to obtain a limited angle tomosynthesis dataset (e.g., processed by applying reconstruction algorithms to the projection image data). In one embodiment, the central x-ray source can also use an anode (e.g., separate additional anode) that can rotate or otherwise move to reduce heat build-up.

Although an exemplary circular arrangement of distributed low power x-ray sources are shown in a number of the figures herein, other linear or non-linear arrangements or even prescribed patterns (e.g., shapes, ellipses, polygons, stars, diamonds, regular or irregular combinations, or repeating patterns) can be used with a corresponding selectable array of collimation windows that can provide combined tomosynthesis and projection x-ray imaging. In one embodiment, a plurality of unit arrays (e.g., 6-8 unit arrays) can be implemented as individual straight line sources that are configured in an arrangement that approximates a circle or other shape.

Figure 9:
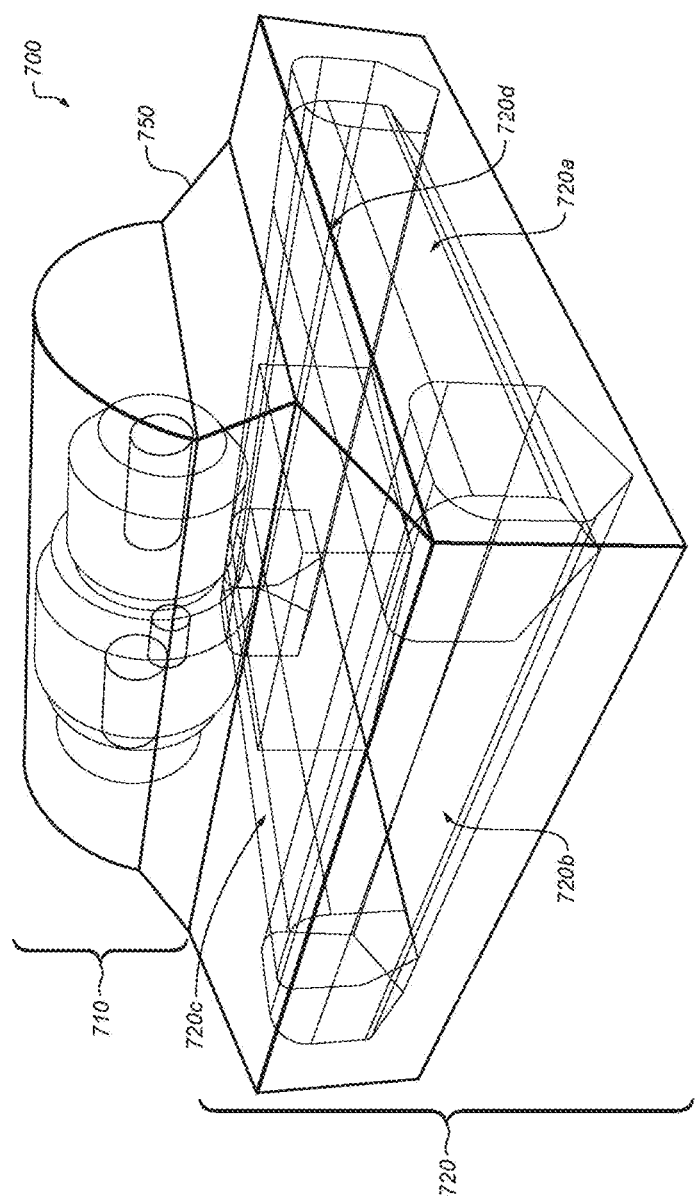
FIG. 9 is a diagram that shows an embodiment of a radiation shield enclosing a combined tomosynthesis and general radiation x-ray source according to embodiments of the application.

In one exemplary embodiment, a standard radiation x-ray source (or at least one distributed source with standard radiation capabilities) can be enclosed in a single radiation shield with a plurality of distributed sources. For example, a carbon-nanotube (CNT) array tube can be packaged along with a traditional tube in the same housing. In one configuration, a single radiation shield enclosing the combination of sources can provide exterior access to the standard radiation x-ray source without disturbing the additional plurality of low power distributed sources. FIG. 9 is a diagram that shows an embodiment of a radiation shield enclosing a combined tomosynthesis and gen rad (e.g., projection x-ray imaging) x-ray source (e.g., x-ray source assembly).

As shown in FIG. 9, a radiation source assembly 700 for radiographic imaging systems and/or methods can implement both projection and tomosynthesis imaging according to embodiments of the application. The radiation source assembly 100 can include a gen rad or first x-ray source 710 to output a beam sufficient for standard projection radiography. The radiation source assembly 700 can include a tomosynthesis imaging source 720 that can be a plurality of groups of distributed sources 720a, 720b, 720c, 720d that can have a prescribed shape. As shown in FIG. 9, the tomosynthesis imaging source 720 can be a plurality of linearly arranged distributed sources 720a, 720b, 720c, 720d that can be configured in a rectangular shape. The radiation source assembly 700 can output x-ray beams to impinge a digital radiographic detector 140. In one embodiment, one or more collimators for the distributed sources 720a, 720b, 720c, 720d can be selectively adjustable between two or more positions, as described previously with reference to FIGS. 5A-5D.

In one exemplary embodiment, the radiation source assembly 700 can include a shared anode for the distributed sources 720a, 720b, 720c, 720d. Further, the embodiment shown in FIG. 9 can use a selectable collimator for the tomosynthesis imaging source and a separate collimator (e.g., fully adjustable) for the general radiation imaging source. Preferably, the standard radiation x-ray source 710 can be enclosed in a single radiation shield 750 with the tomosynthesis imaging source 720 (e.g., groups of distributed sources 720a, 720b, 720c, 720d). In one embodiment, access can be provided through the single radiation shield 750 to the standard radiation x-ray source 710 without impacting a portion of the radiation shield 750 for the tomosynthesis imaging source 720. In one embodiment, access can be provided through the single radiation shield 750 to the tomosynthesis imaging source 720 (e.g., 720a) without impacting a portion of the radiation shield 750 for the standard radiation x-ray source 710. In one embodiment, the groups of distributed sources 720a, 720b, 720c, 720d can be independently adjusted or have different relative positions relative to a detector upon which corresponding beam shaped emissions will impinge. Collimator plate assembly 122 or other collimators for the distributed sources 720a-720d can be within or outside radiation shield 750.

Outlining the Radiation Field

Embodiments of the present disclosure provide a visual mechanism for indicating the extent of the radiation field for the distributed array sources 120. In addition, certain embodiments of the present disclosure indicate the extent of the radiation field for the radiography radiation source, where used, as well as for peripheral distributed sources 120. Visible illumination is used to demarcate the cross-sectional extent and shape of radiation fields 152 as they relate to the surface of the radiographic detector.

Figure 10A:
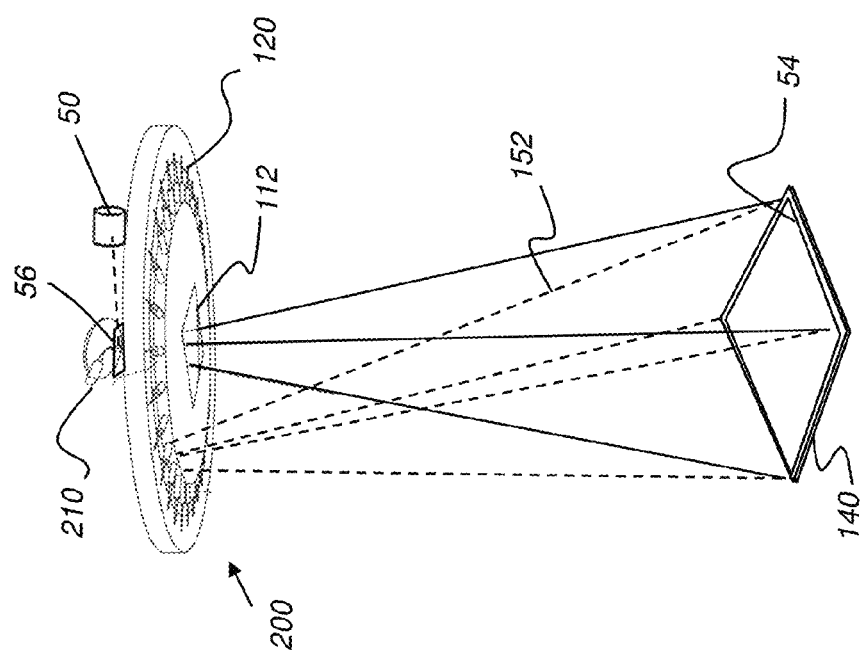
FIG. 10A is a schematic diagram that shows how the radiation field can be indicated using an illumination source.

Referring to FIG. 10A, radiation source assembly 200 has an illumination source 50 and a reflector 56, wherein the light source is energizable to project light onto detector 140, wherein the projected light indicates the cross-sectional shape of radiation field 152 for any source 120 in the collimated subset of distributed sources 120 that is to be used for obtaining image content. An outline 54 formed by the edges of the illumination displays on or at the position of detector 140 and shows the extent of the field 152 on detector 140. Processor 20 (FIG. 2C) provides this indication by using blade collimator 112 of the radiography radiation source 210. Based on the calculated radiation field dimensions for the subset of distributed sources 120 that will be used, processor 20 provides the needed signals to adjust the blade collimator 112 opening. Illumination source 50 is energized to direct light through the blade collimator 112 aperture at a suitable opening and angle for marking the boundaries of the radiation field on the detector.

In order to perform the needed calculation for identifying the aspect ratio and dimensions of the radiation field that will be generated, processor 20 determines which subset of distributed sources 120 are to be used, one at a time, for the tomosynthesis imaging. This can be a predetermined subset of sources 120, or a subset of sources 120 that are specified by user instructions. Processor 20 then obtains data from default information or from other sensors in the system as to the source-detector distance (SID). Collimator information from collimator plate assembly 122 then determines the angular extent of the collimated beam and the corresponding area to be imaged. Where blade collimator 112 is used to define the edges of light, the blade collimator 112 is then opened to the appropriate size for indicating the radiation field according to the geometry of illumination source 50 position, collimator 112 setting, and detector 140 position.

Figure 10B:
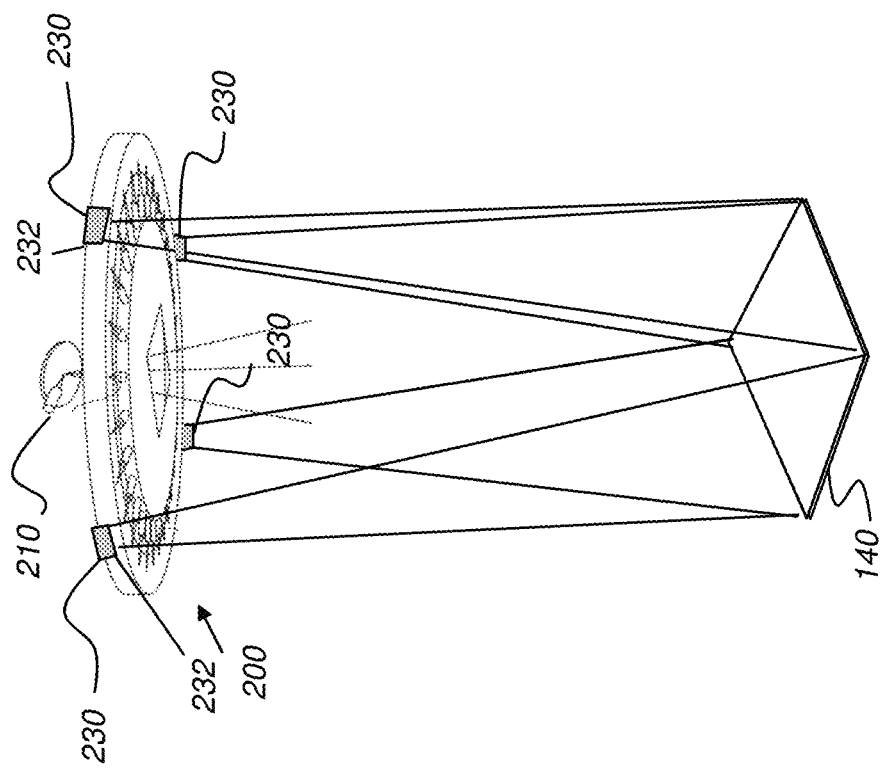
FIG. 10B is a schematic diagram that shows how the radiation field can be indicated using line LED or line laser sources.

FIG. 10B is a schematic diagram that shows how the radiation field for a circular distributed source array can be indicated using line LED or line laser sources, shown as a set of solid-state light sources 230. To mark the four sides of the collimated radiation field directed toward the rectangular detector 140 shown in FIG. 10B, four solid-state light sources 230 are used. In order to accurately define the edges of the collimated field, processor 20 (FIG. 2C) can identify the collimator type that is used and the distributed x-ray sources 120 that will be employed. An actuator 232 is provided with each light source 230, capable of tilting the light source 230 to adjust for line position, according to instructions based on calculations performed at processor 20.

Where the radiation source array is substantially linear, light sources 230 can be similarly mounted along edges of the collimator member 94, as shown in FIG. 6D.

According to an alternate embodiment of the present disclosure, one or more solid-state light sources is provided on collimator member 94 and is aligned so that it indicates the radiation field outline for a particular SID and aperture arrangement. Thus, for example, multiple solid-state light sources 230 can be provided on collimator member 94, as shown in FIG. 6E and the appropriate source 230 energized by processor 20 (FIG. 2C) based on SID and aperture geometries. Light sources 230 can alternately be coupled to some other portion of radiation source assembly 200.

Illumination source 50 (FIG. 10A) can be any of a number of types of light sources. Solid-state light sources, such as LED or laser arrays, can be particularly well-adapted to respond as illumination source 50. According to an embodiment of the present disclosure illumination source 50 can be a line LED or line laser, as described with reference to FIG. 10B. For this arrangement, illumination source 50 can be coupled to collimator 112 or to some other component of radiation source assembly 200.

Collimator plate assembly 122 can be positioned and translated between positions with respect to distributed sources 120 in any of a number of ways. Collimator plate assembly 122 can be rotated or translated into different positions according to which sources 120 need to be collimated for obtaining a particular image. Within some limits defined by system geometry, collimator plate assembly 122 can also be moved closer to or further from the sources 120 in order to vary the shape of the collimated radiation field, as described previously with respect to FIGS. 6H and 6I. Collimator plate assembly 122 can be planar or curved and may have some of its apertures 222 in a different plane than others. Thus, for example, a first subset of apertures 222 can be in a first plane nearest the array of distributed sources 120 and a second set of apertures 222 in a second plane spaced apart from the first plane and farther from the array of distributed sources 120.

Collimator plate assembly 122 can have multiple components, such as two or more apertured plates that may or may not be mechanically coupled and cooperate to provide the needed combination of sources and radiation field for multiple projection images. In addition, it should be noted that two or more distributed source 120 arrays can be used, each source 120 array provided with a corresponding collimator. By implementing a distributed source in several smaller pieces, certain exemplary embodiments can include some measure of independent movement of the plurality of arrays of distributed sources 120. For example, one exemplary embodiment can include a configuration that can make the source 120 arrays (e.g., four arms) independently adjustable or able to move separately. Thus, individual source 120 arrays or opposite arrays can move outward to provide a wider angular coverage to improve in plane or out of plane resolutions. To allow this type of flexibility, collimator apparatus can be provided for each individual array.

Virtual Collimator Mask

Because there can be a number of variables related to sizing and positioning of the radiation field, there can be areas of the detector that lie outside the exposure beams provided from the imaging apparatus. When this happens, it is useful to identify portions of the detector that lie outside the collimation radiation field and are therefore unexposed, so that data for corresponding image pixels in unexposed areas are not used in tomosynthesis reconstruction processing.

Figure 11A:
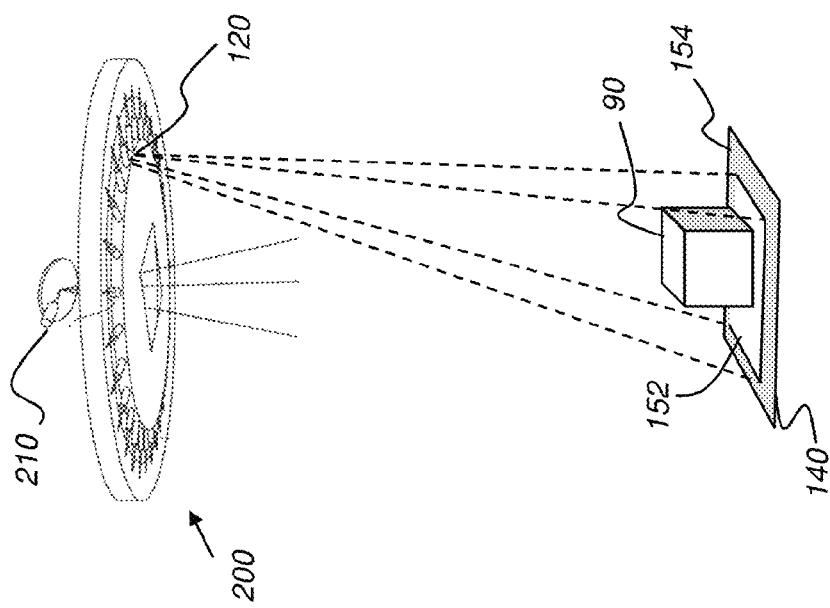
FIG. 11A is a schematic diagram that shows an example in which portions of the detector are not exposed and their corresponding pixel data should not be used for reconstruction.

The schematic diagram of FIG. 11A shows an example in which portions of the detector are not exposed and their corresponding pixel data should not be used for reconstruction. A projection image of an object 90 is acquired with a radiation field 152 that does not fully extend from edge to edge on detector 140. There is an unused, unexposed portion 154 of detector 140 that receives no x-ray radiation. If the corresponding pixel image data were used in reconstruction calculations, image artifacts would be likely. This is because the reconstruction calculations assume (i) that all receiver pixels lie within the radiation field and (ii) that the data acquired from unexposed portion 154 indicate high attenuation, rather than showing that this area was outside the radiation field.

Figure 11B:
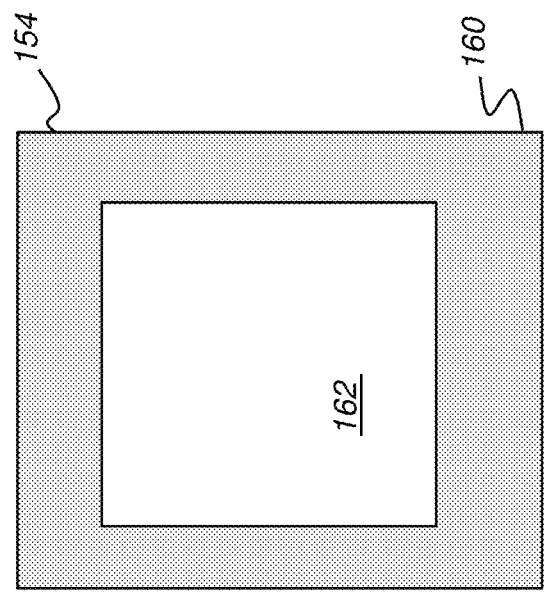
FIG. 11B is a plan view that shows portions of a collimation mask for tomosynthesis imaging.

In order to eliminate pixels in unexposed portion 154 from reconstruction calculations, embodiments of the present disclosure provide a virtual collimator mask, as shown in the plan view of FIG. 11B. A collimator mask 160 defines those pixels of the image that are used for image reconstruction and those that are not used. Collimator mask 160 thus effectively removes image data from unreachable areas of the digital detector where tomosynthesis is performed. Collimator mask 160 defines an image area 162 and unused, unexposed portion 154.

The collimator masking process uses a projection model that includes positional, angular, and inter-distance information on the distributed x-ray sources 120 and detector. The projection model can also include collimator plate assembly 122 dimensional and positional data that can identify image data that corresponds to unexposed portions 154 of detector 140 and should be removed from reconstruction calculations. Calculations needed for determining the dimensions of image area 162 and unexposed portion 154 can be complicated by the varying geometry of different x-ray sources that are used in the array. Thus, some adjustment of the boundary for the image area 162 may need to be computed in order to compensate for uncertainty, such as where it may not be clear whether or not particular pixels lie within the image area 162. Mask sizing can be computed dynamically for each tomosynthesis session. Alternately, data for mask sizing and registration can be stored in memory accessible to processor 20 (FIG. 2C).

Figure 12:
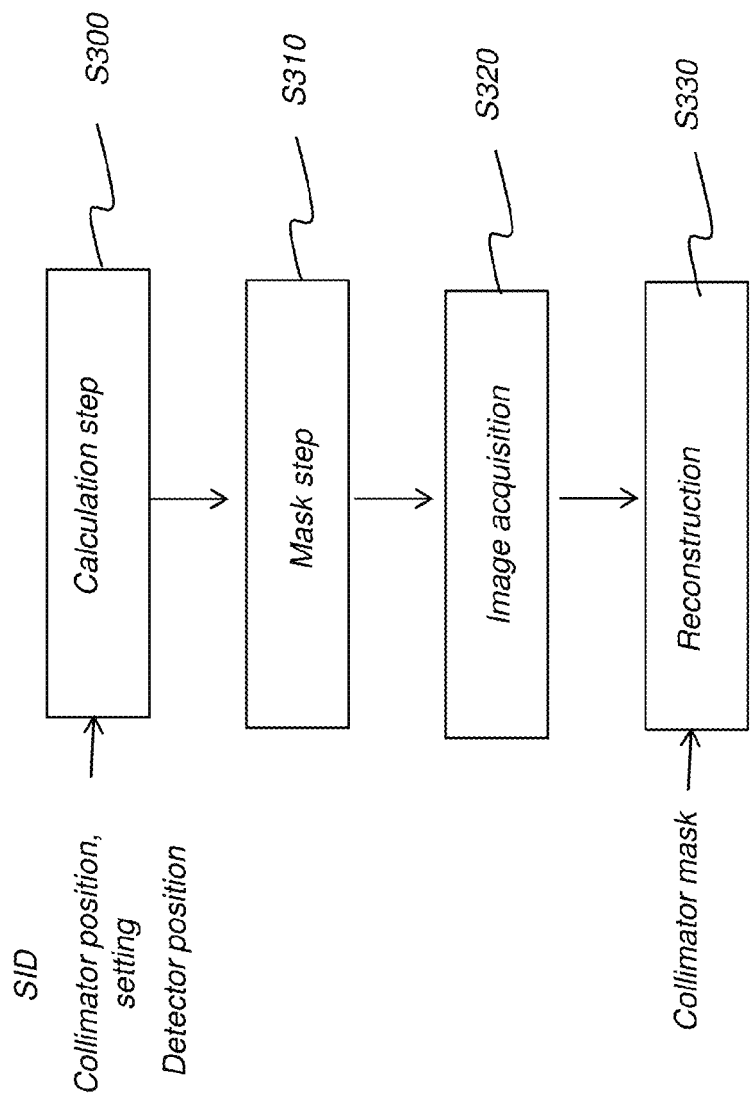
FIG. 12 is a logic flow diagram that shows the sequence for reconstruction when using a mask.

Referring to FIG. 12, there is shown a logic flow sequence for calculating and using the collimator mask 160 of FIG. 11B. Input information for the process include the SID, collimator position and aperture data such as size, and detector position. A calculation step S300 calculates the extent of the available radiation field with respect to the detector. A mask step S310 defines which image content for each projection image will be considered in the tomosynthesis reconstruction. Image data is acquired during an image acquisition step S320. Reconstruction processing in volume reconstruction step S330 then applies data defined by the collimator mask and thus avoids using misleading data from areas of the detector that lie outside the radiation field, shown as unexposed portions 154 in FIGS. 11A and 11B.

Exemplary embodiments according to the application can include various features described herein (individually or in combination). It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

For exemplary functions described herein and/or performed as described with reference to the figures, the system processor 20 (FIG. 2C) or the radiographic imaging system/unit may be implemented, for example, but not limited to using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), GPU, video digital signal processor (VDSP) and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software is generally executed from a medium or several media by one or more of the processors of the machine implementation.

Consistent with one embodiment, the present invention utilizes a computer program with stored instructions that control system functions for image acquisition and image data processing for image data that is stored and accessed from an electronic memory. As can be appreciated by those skilled in the image processing arts, a computer program of an embodiment of the present invention can be utilized by a suitable, general-purpose computer system, such as a personal computer or workstation that acts as an image processor. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A radiographic imaging apparatus comprising:
   a radiation detector;
   a radiation source array having a plurality of radiation sources;
   a control processor configured to sequentially and separately energize a selected two or more of the plurality of radiation sources;
   a collimator movable to either a first position or a second position in a path of radiation from an energized one of the plurality of radiation sources, the collimator having a plurality of apertures wherein, when the collimator is at the first position, the plurality of apertures are aligned with a first subset of the radiation sources to define a first radiation field on the radiation detector, and when the collimator is at the second position the plurality of apertures are aligned with a second subset of the radiation sources to define a second radiation field on the radiation detector, and wherein the first and second radiation fields are substantially the same; and
   a transport apparatus that is energizable to move the collimator between at least the first and the second positions.

2. The apparatus of claim 1, wherein the collimator comprises a plate having a plurality of rectangular apertures therethrough.

3. The apparatus of claim 2, wherein the rectangular apertures each comprises a different aspect ratio.

4. The apparatus of claim 2, wherein the collimator comprises a curved plate.

5. The apparatus of claim 1, wherein the collimator comprises two adjacent parallel metal plates, the apertures aligned with the first subset of radiation sources are disposed in a first one of the metal plates, and wherein the apertures aligned with the second subset of radiation sources are disposed in a second one of the metal plates.

6. The apparatus of claim 1, wherein the first and second subsets of the radiation sources in the array are disjoint subsets.

7. The apparatus of claim 1, wherein each of the plurality of radiation sources that is blocked by the collimator from emitting x-rays toward a subject when the collimator is at the first position is adjacent to at least one radiation source of the plurality of radiation sources that is not blocked from emitting x-rays toward the subject when the collimator is at the second position.

8. The apparatus of claim 1, wherein the plurality of radiation sources are arranged in a substantially circular array.

9. A radiographic imaging apparatus comprising:
  a radiographic energy detector;
  a central radiographic energy source comprising:
    (i) an x-ray generator; and
    (ii) a collimator positioned adjacent the generator to direct central radiation from the generator toward a first radiation field on the detector;
  an array of peripheral radiation sources that are disposed about a periphery of the central radiographic energy source;
  a collimator assembly having a central opening for the central radiation to pass therethrough, and a plurality of peripheral apertures each of which is aligned with one of the peripheral radiation sources, the collimator assembly rotatable to a first position and a second position, wherein, when the collimator assembly is rotated to the first position, a first one of the peripheral radiation sources is aligned with a first one of the apertures to emit collimated radiation toward the radiation detector through the first one of the apertures, and wherein, when the collimator assembly is rotated to the second position, a second one of the peripheral radiation sources is aligned with the first one of the apertures to emit collimated radiation to the radiation detector through the first one of the apertures.

10. The apparatus of claim 9, wherein the peripheral radiation sources each comprise a carbon nanotube cathode x-ray source.

11. The apparatus of claim 9, wherein the peripheral radiation sources are arranged in an octagonal pattern in a common plane.

12. The apparatus of claim 9, wherein the collimator assembly is configured to align the plurality of the peripheral apertures each with one of a first subset of the array of peripheral radiation sources and to block each of a second subset of the array of peripheral radiation sources when the collimator assembly is rotated to the first position, and wherein the collimator assembly is configured to align the plurality of the peripheral apertures each with one of the second subset of the array of peripheral radiation sources and to block each of the first subset of the array of peripheral radiation sources when the collimator assembly is rotated to the second position.

13. The apparatus of claim 12, wherein the first and second positions of the collimator assembly are 180 degrees apart.

14. The apparatus of claim 9, wherein the collimator assembly comprises a pair of metal plates each having apertures therethrough, and wherein the apertures of one of the metal plates are aligned with the apertures of the other metal plate when the collimator assembly is rotated to either of the first or second positions.

15. The apparatus of claim 9, wherein, when the collimator assembly is rotated to a third position, a third one of the peripheral radiation sources is aligned with the first one of the apertures to emit collimated radiation toward the radiation detector through the first one of the apertures.

16. The apparatus of claim 15, wherein the first and second rotational positions of the collimator assembly are 45 degrees apart, and wherein the second and third rotational positions of the collimator assembly are 45 degrees apart.

17. A radiographic imaging apparatus comprising:
  a radiation detector;
  a radiation source array having a plurality of radiation sources;
  a control processor configured to individually and sequentially energize two or more of the plurality of radiation sources in the radiation source array;
  a collimator member movable to be disposed at either a first position or a second position in a path of the radiation source array and having a plurality of apertures,
  wherein, with the collimator member at the first position, the plurality of apertures are aligned with a first subset of the radiation sources in the array and define a radiation field on the radiation detector,
  and wherein, with the collimator member at the second position, the plurality of apertures are aligned with a second subset of the radiation sources in the array, different from the first subset by at least one member, and
  wherein the second subset of the radiation sources propagate radiation along substantially a same radiation field as the first subset of the radiation sources when the collimator member is in the first position;
  a transport apparatus that is energizable to translate the collimator member between at least the first and second positions according to an instruction from the control processor; and
  a solid-state light source coupled to the source array or to the collimator member, the light source energizable to illuminate the radiation field on the detector.

18. The apparatus of claim 17, wherein the solid-state light source includes a line LED or line laser.

19. The apparatus of claim 17, wherein the radiation source array is substantially linear.

20. The apparatus of claim 17, further comprising a plurality of solid-state light sources coupled to the source array or to the collimator member, wherein a first one of the plurality of solid-state light sources is energized when the collimator member is at the first position, and wherein a second one of the solid-state light sources is energized when the collimator member is at the second position.

* * * * *